United States Patent [19]

Stirling et al.

[11] 4,435,565

[45] Mar. 6, 1984

[54] 9-DEOXY-9-AMINO-CLAVULANATE ANTIBACTERIAL AGENTS

[75] Inventors: Irene Stirling, Reigate; Brian P. Clarke, Kingswood, both of England

[73] Assignee: Beecham Group Limited, England

[21] Appl. No.: 244,098

[22] Filed: Mar. 16, 1981

Related U.S. Application Data

[60] Division of Ser. No. 95,799, Nov. 19, 1979, which is a continuation of Ser. No. 896,441, Apr. 14, 1978, abandoned.

[30] Foreign Application Priority Data

Apr. 22, 1977 [GB] United Kingdom ............... 16764/77
Sep. 6, 1977 [GB] United Kingdom ............... 37072/77
Dec. 2, 1977 [GB] United Kingdom ............... 50229/77
Dec. 23, 1977 [GB] United Kingdom ............... 53866/77

[51] Int. Cl.$^3$ .................... C07D 487/04; A61K 31/42
[52] U.S. Cl. ................................. 542/416; 260/245.3; 424/272
[58] Field of Search ..................................... 260/245.3

[56] References Cited

U.S. PATENT DOCUMENTS 4,256,638 3/1981 Ponsford .......................... 260/245.3
4,258,050 3/1981 Harbridge ........................ 260/245.3

*Primary Examiner*—Mark L. Berch
*Attorney, Agent, or Firm*—Jacobs & Jacobs

[57] ABSTRACT

Secondary amines of clavulanic acid are useful as beta-lactamase inhibitors that enhance the effectiveness of penicillins or cephalosphorins and also have antibacterial properties in their own right.

8 Claims, No Drawings

9-DEOXY-9-AMINO-CLAVULANATE ANTIBACTERIAL AGENTS

This is a division of Ser. No. 95,799 filed Nov. 19, 1979 which is a continuation of Ser. No. 896,441 filed Apr. 14, 1978, abandoned.

The present invention relates to β-lactam antibacterial agents, to the process for their preparation and to compositions containing them.

U.S. Ser. No. 731,928 and Belgian Pat. No. 847044 disclose inter alia the compounds of the formula (I):

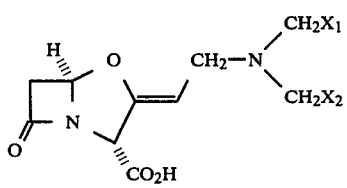

and esters thereof wherein $X_1$ is hydrogen atom, an alkyl group of up to 5 carbon atoms, an alkenyl group of up to 5 carbon atoms, a hydroxy alkyl group of up to 5 carbon atoms or an optionally substituted phenyl group and $X_2$ is an optionally substituted phenyl group, such compounds were described as antibacterial agents and β-lactamase inhibitors.

It has now been discovered that certain secondary amines can be prepared that are β-lactamase inhibitors that enhance the effectiveness of penicillins or cephalosporins and which also have antibacterial properties in their own right.

The present invention provides a compound of the formula (II):

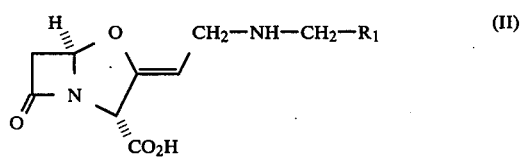

or an ester thereof wherein $R_1$ is a hydrogen atom, an alkyl group of up to 5 carbon atoms, a cycloalkyl group of 5 or 6 carbon atoms, a hydroxyalkyl group of up to 5 carbon atoms or a moiety of the sub-formula (a):

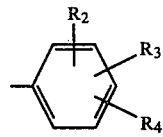

wherein $R_2$ is a hydrogen, fluorine, chlorine or bromine atom or an alkyl group of 1–3 carbon atoms, an alkoxyl group of 1–3 carbon atoms, an acyloxy group of 1–3 carbon atoms, a hydroxyl group, and alkoxycarbonyl group containing 1–3 carbon atoms in the alkoxy part, or a group $-N(R_5)CO.R_6$, $-N(R_5)SO_2R_6$ or $-CO-NR_5R_6$ where $R_5$ is a hydrogen atom or an alkyl group of 1–3 carbon atoms or a phenyl or benzyl group and $R_6$ is an alkyl group of 1–3 carbon atoms or a phenyl or benzyl group; $R_3$ is a hydrogen, fluorine or chlorine atom or an alkyl group of 1–3 carbon atoms, an alkoxy group of 1–3 carbon atoms or an acyloxyl group of 1–3 carbon atoms; and $R_4$ is a hydrogen fluorine or chlorine atom or an alkyl group of 1–3 carbon atoms or an alkoxy group of 1–3 carbon atoms.

The compounds of the formula (II) per se exist in the form of zwitterions, that is they may be represented as shown in formula (IIa):

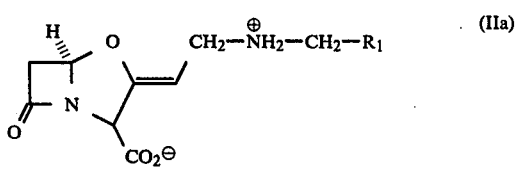

if desired wherein $R_1$ is as defined in relation to formula (II). These zwitterionic compounds form a favoured aspect of this invention in view of their generally crystalline form and their greater stability than previously reported β-lactamase inhibitory amines such as those of the formula (I).

The esters of the compounds of the formula (II) may be presented in the form of the free base or in the form of an acid addition salt.

Suitably $R_1$ is a hydrogen atom. Suitably $R_1$ is an alkyl group of up to 5 carbon atoms. Suitably $R_1$ is a hydroxyalkyl group of up to 5 carbon atoms. Suitably $R_1$ is a phenyl group optionally substituted by a fluorine, chlorine or bromine atom or an alkyl or alkoxy group of up to 3 carbon atoms.

Apt groups $R_1$ include the methyl, ethyl, propyl, butyl, hydroxymethyl, hydroxyethyl, hydroxypropyl, phenyl, p-methoxyphenyl, p-methylphenyl and the like groups. Certain particularly apt groups $R_1$ include the methyl, ethyl hydroxymethyl, 2-hydroxyethyl, isopropyl and phenyl groups.

A group of suitable compounds of this invention are those of the formula (II) or an ester thereof wherein $R_1$ is a hydrogen atom an alkyl group of up to 5 carbon atoms, a hydroxyalkyl group of up to 5 carbon atoms or a moiety of the sub-formula (b):

wherein $R_2$ is a hydrogen, fluorine, chlorine or bromine atom or an alkyl group of 1–3 carbon atoms, an alkoxyl group of 1–3 carbon atoms, an acyloxy group of 1–3 carbon atoms, a hydroxyl group or an alkoxycarbonyl group containing 1–3 carbon atoms in the alkoxy part; $R_3$ is a hydrogen, fluorine or chlorine atom or an alkyl group of 1–3 carbon atoms, an alkoxy group of 1–3 carbon atoms or an acyloxyl group of 1–3 carbon atoms; and $R_4$ is a hydrogen, fluorine or chlorine atom or an alkyl group of 1–3 carbon atoms or an alkoxy group of 1–3 carbon atoms. As described above these compounds may be in the form of the zwitterion or an ester or an acid addition salt of said ester. Suitable and apt values for $R_1$ include those set forth hereinbefore in relation to formula (II).

One favoured sub-group of compounds within formula (II) include those of the formula (III):

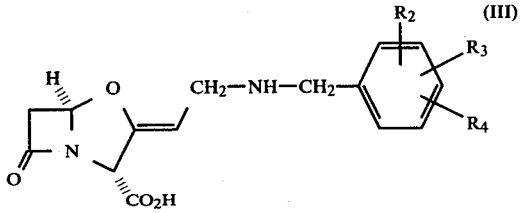

and esters thereof wherein $R_2$, $R_3$ and $R_4$ are as defined hereinbefore.

These compounds of the formula are favourably in the form of the zwitterion for reasons hereinbefore indicated. The compounds of the formula (III) may be presented in the form of the ester and suitably that ester is in the form of its acid addition salt.

More suitably $R_2$ is a hydrogen, fluorine or chlorine atom or a methoxyl, ethoxyl, hydroxyl, acetoxyl, propionyloxy, methyl, ethyl, methoxycarbonyl or ethoxycarbonyl group.

More suitably $R_3$ is a hydrogen, fluorine or chlorine atom or a methoxyl, ethoxyl, acetoxyl, propionoxyl, methyl or ethyl group.

More suitably $R_4$ is a hydrogen, fluorine or chlorine atom or a methoxyl, ethoxyl, acetoxyl, propionoxyl, methyl or ethyl group.

Most suitably $R_2$ is a hydrogen, fluorine or chlorine atom or a methoxyl, hydroxyl or methyl group.

Most suitably $R_3$ is a hydrogen, fluorine or chlorine atom or a methoxyl or methyl group.

Most suitably $R_4$ is a hydrogen atom or a methyl or methoxyl group.

Preferably $R_2$ is a hydrogen, fluorine or chlorine atom or a methyl or methoxyl group.

Preferably $R_3$ is a hydrogen atom or methoxyl group.

Preferably $R_4$ is a hydrogen atom.

The compounds of this invention and particularly those of the formula (III) show a broad spectrum of β-lactamase inhibitory activity.

Certain particularly favoured compounds of the formula (III) include those of the formula (IV):

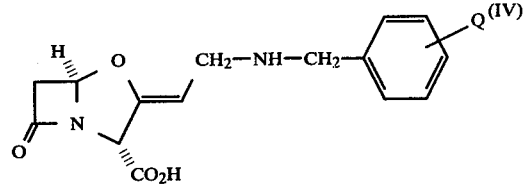

wherein Q is a hydrogen, fluorine or chlorine atom or a methyl, methoxyl, ethyl or ethoxyl group.

Suitably Q is a hydrogen, p-fluorine, m-fluorine, p-chlorine or m-chlorine atom or a p-methyl, m-methyl, p-methoxyl or m-methoxyl group.

Most suitably Q is a hydrogen, p-fluorine or p-chlorine atom or a p-methyl or p-methoxyl group.

A compound of the formula (IV) which has shown particularly good synergistic activity in-vivo is that wherein Q is a hydrogen atom. This compound is able to enhance the effectiveness of penicillins, such as ampicillin or amoxycillin, and cephalosporins against various β-lactamase producing strains of gram-negative bacteria including strains of *Klebsiella aerogenes, Escherichia coli, Proteus mirabilis* and the like and especially against β-lactamase producing strains of gram-positive bacteria such as *Staphylococcus aureus* when administered orally and especially when administered by injection. The compounds of the formula (IV) also have an advantageously low acute toxicity, for example no deaths in test animals were observed when administering therapeutic amounts of the synergist. In addition such compounds are effective when used alone in treatment of infections due to β-lactamase producing as well as non-β-lactamase producing strains of *Staphylococcus aureus*. Thus, for example, the compound of the formula (IV) wherein Q is a hydrogen atom has proved more effective than ampicillin, cloxacillin or cefazolin in treating certain infections due to *Staphylococcus aureus* Russell.

A further favoured sub-group of compound within formula (II) having similar properties to that of the sub-group of the formula (IV) is that of the formula (V):

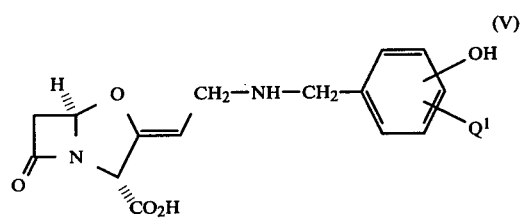

wherein $Q^1$ is a hydrogen, fluorine or chlorine atom or a methyl, ethyl, methoxyl, ethoxyl or hydroxyl group.

Suitably the OH substituent shown in formula (VIa) is para- to the carbon to which the —NH—CH$_2$— moiety is attached.

Suitably the OH substituent shown in formula (VIa) is meta- to the carbon atom to which the —NH—CH$_2$— moiety is attached.

Most suitably $Q^1$ is a hydrogen atom or a methyl or methoxy group.

The zwitterionic compounds of the formula (IV) and (V) are normally and preferably in crystalline form.

A further sub-group of favoured compounds of this invention are those of the formula (II) wherein $R_2$ is a group $N(R_5)CO.R_6$, $N(R_5)SO_2R_6$ or $CONR_5R_6$ wherein $R_5$ and $R_6$ are as defined in relation to formula (II) and esters thereof. Suitably $R_5$ is a hydrogen atom. Suitably $R_5$ is an alkyl group of 1–3 carbon atoms such as the methyl group. Suitably $R_6$ is an alkyl group of 1–3 carbon atoms. More suitably $R_6$ is a methyl group. Suitable values for $R_3$ and $R_4$ in such compounds are those specified in relation to the compounds of the formula (II). Such compounds may be in the form of zwitterions of the parent acid. Esters of such compounds may be in the form of the free base or may be in the form of an acid addition salt.

A further particularly favoured sub-group of the compounds of the formula (II) is that of the formula (VI):

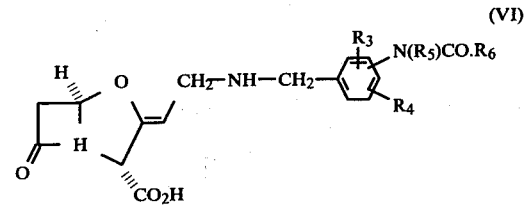

wherein $R_3$, $R_4$, $R_5$ and $R_6$ are as defined in relation to formula (II).

The compounds of the formula (VI) are generally produced in crystalline form and in better than average yield and have similar activity to those of the formula (IV) and (V).

In relation to the compounds of formula (VI) it is more suitable that $R_5$ is a hydrogen atom or an alkyl group of 1–3 carbon atoms such as a methyl group and most suitably $R_5$ is a hydrogen atom. In relation to the compounds of the formula (VI) it is more suitable that $R_6$ is an alkyl group of 1–3 carbon atoms such as the methyl group.

Favoured values for $R_3$ and $R_4$ for the compounds of the formula (VI) are as defined in relation to formulae (II) and (III). Preferably $R_3$ and $R_4$ are both hydrogen atoms.

Suitably in the compounds of the formula (VI) the —$N(R_5)COR_6$ moiety is attached para to the —NH—$CH_2$— moiety.

Suitably in the compounds of the formula (VI) the —$N(R_5)COR_6$ moiety is attached meta to the —NH—$CH_2$— moiety.

A favoured sub-group of compounds of the formula (VI) are those of the formula (VII):

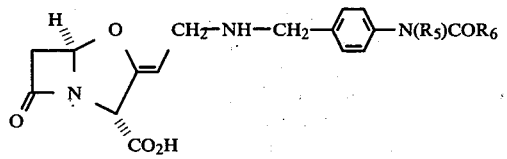

(VII)

wherein $R_5$ and $R_6$ are as defined in relation to formula (II). Particularly suitably $R_5$ is a hydrogen atom or an alkyl group of 1–3 carbon atoms such as a methyl group. Preferably $R_5$ is a hydrogen atom. Particularly suitably $R_5$ is an alkyl group of 1–3 carbon atoms and preferably a methyl group.

As has been previously indicated we prefer to prepare and use the crystalline zwitterionic compounds within formula (II) such as those of the formulae (III), (IV), (V), (VI) and (VII) and the like. However, esters of the compounds of the formulae (II)–(VII) also form part of this invention, for example as the free base or as the acid addition salt, since such compounds may also be used to enhance the effectiveness of penicillins or cephalosporins.

Certain suitable esters of the compounds of the formula (II)–(VII) include those of the formula (VIII) and (IX):

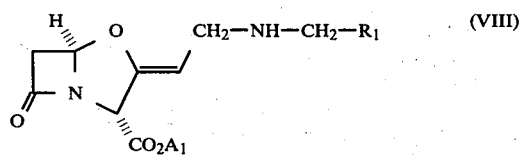

(VIII)

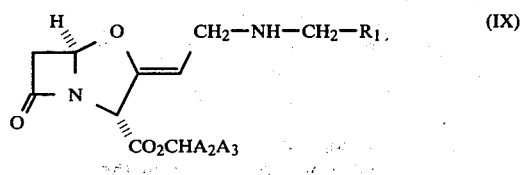

(IX)

wherein $R_1$ is as defined in relation to formula (II) or is a substituted phenyl group as present in a compound of the formula (III)–(VII) wherein $A_1$ is an alkyl group of 1–6 carbon atoms optionally substituted by an alkoxyl or acyloxyl group of 1–7 carbon atoms; $A_2$ is an alkenyl or alkynyl group of up to 5 carbon atoms or is a phenyl group optionally substituted by a fluorine, chlorine, bromine, nitro or alkyl or alkoxy of up to 4 carbon atoms; and $A_3$ is a hydrogen atom, an alkyl group of up to 4 carbon a atoms or a phenyl group optionally substituted by a fluorine, chlorine, bromine, nitro or alkyl or alkoxyl of up to 4 carbon atoms.

Suitable esters of the compounds of the formula (II) include the methyl, ethyl, n-propyl, n-butyl, allyl, $CH_2$—C≡CH, methoxymethyl, acetoxymethyl, propionoxymethyl, pivaloyloxymethyl, ethoxycarbonyloxymethyl, methoxycarbonyloxyethyl, ethoxycarbonyloxyethyl, dimethoxyphthalidyl, benzyl, methoxybenzyl, ethoxybenzyl, nitrobenzyl, chlorobenzyl or the like ester.

Certain favoured groups $A_1$ include the methyl, methoxymethyl, acetoxymethyl, acetoxyethyl, phthalidyl, ethoxycarbonyloxymethyl, α-ethoxycarbonyloxyethyl and the like groups.

Certain favoured groups $A_2$ include the phenyl and 4-methoxyphenyl groups. A particularly favoured moiety $A_3$ is the hydrogen atom.

Certain other favoured values for $A_1$ include those of the sub-formulae (c), (d) and (e):

| | |
|---|---|
| —$CHA_5$—$OA_6$ | (c) |
| —$CHA_5$—$COA_6$ | (d) |
| —$CHA_5$—$CO_2A_6$ | (e) | wherein $A_5$ is a hydrogen atom or a methyl group and $A_6$ is an alkyl group of up to 4 carbon atoms or a phenyl or benzyl group either of which may be substituted by one or two alkyl or alkoxyl group of up to 3 carbon atoms or by a fluorine, chlorine or bromine atom or a nitro group; or $A_5$ is joined to $A_6$ to form the residue of an unsubstituted saturated 5- or 6-membered heteroalicyclic ring or an ortho-phenylene group which may be substituted by one or two alkyl or alkoxy groups of up to 3 carbon atoms or by a fluorine, chlorine or bromine atom or nitro group.

An apt acylic value for the sub-group of the formula (c) is —$CH_2$—$OA_6$.

An apt acylic value for the sub-group of the formula (d) is —$CH_2$—CO—$A_6$.

An apt acylic value for the sub-group of the formula (e) is —$CH_2$—$CO_2A_6$.

A further apt acylic value for the sub-group of the formula (e) is —$CH(CH_3)$—$CO_2A_6$.

Favoured values for $A_6$ in the preceding acylic moieties include the methyl, ethyl, propyl, butyl, phenyl and benzyl groups.

Apt cyclic values for the sub-group of the formula (c) include the tetrahydropyranyl and tetrahydrofuranyl groups.

Esters of the compounds of the formula (II) such as those of the compounds of the formulae (IV) or (V) may be presented in the form of their acid addition salts if desired. The acid used to form the salt will most suitably be pharmaceutically acceptable, but non-pharmaceutically acceptable acid addition salts are also envisaged, for example an intermediates in the preparation of the pharmaceutically acceptable salts by ion exchange. Suitable pharmaceutically acceptable acid addition salts include those of inorganic and organic acids, such as hydrochloric, phosphoric, sulphuric, methanesulphonic, toluenesulphonic, citric, malic, acetic, lactic, tartaric, propionic, succinic or the like acid. Most suitably the acid addition salt is provided as a solid and preferably as a crystalline solid.

Compounds of this invention wherein crystalline form may be solvated, for example hydrated.

The present invention provides a pharmaceutical composition which comprise a compound of this invention and a pharmaceutically acceptable carrier.

The compositions of the invention include those in a form adapted for oral, topical or parenteral use and may be used for the treatment of the infection in mammals including humans.

Suitable forms of the compositions of this invention include tablets, capsules, creams, syrups, suspensions, solutions, reconstitutable powders and sterile forms suitable for injections or infusion. Such compositions may contain conventional pharmaceutically acceptable materials such as diluents, binders, colours, flavours, preservatives, disintegrant and the like in accordance with conventional pharmaceutical practice in the manner well understood by those skilled in the art of formulating antibiotics.

Injectable or infusable compositions of a compound of the invention are particularly suitable as high blood levels of the compound can occur after administration by injection or infusion. Thus, one preferred composition aspect of this invention comprises a compound of the invention in sterile form and most suitably in sterile crystalline form. The zwitterionic compounds of this invention are particularly suitable for use in such compositions.

The injectable solution of the compound of this invention may be made up in a sterile pyrogen-free liquid such as water, aqueous ethanol or the like.

Compounds of this invention when in highly pure crystalline form tend to have relatively low aqueous solubilities so that if it is desired to administer substantial quantities of the medicament this can require fairly large quantities of water for reconstitution. In these circumstances it is often convenient to administer the solution intravenously.

An alternative approach to administering the compounds of this invention and especially those zwitterionic compounds of the formula (III)–(VII) is to utilise an injectable suspension. Such suspensions may be made up in sterile water; sterile saline or the like and may also contain suspending agents such as polyvinylpyrrolidone, lecithin or the like (for example in the manner described for amoxycillin trihydrate in Belgian Pat. No. 839109). Alternatively such compositions may be prepared in an acceptable oily suspending agent such as arachis oil or its equivalent. The use of suspensions can give rise to advantageously prolonged blood levels of the medicament. Belgian Pat. No. 839109 may be consulted for suitable methods and materials for producing injectable aqueous suspensions. For use in such suspensions the zwitterionic compound of this invention should be in the form of fine particles as described in said Belgian Patent.

Unit dose compositions comprising a compound of this invention adapted for oral administration form a further suitable composition aspect of this invention. However, orally administrable forms are generally less favoured than injectable forms owing to the relatively poor absorption of the compounds from the gastro-intestinal tract. Despite this orally administrable compositions are of use as a synergistically effective blood level can be expected at high doses and at lower doses such compositions may be used to treat infections localised in the gastro-intestinal tract.

Unit dose compositions comprising a compound of this invention adapted for topical administration are also presented by this invention. In this instance 'topical administration' also includes local administration to internal surfaces of mammary glands of cattle, for example during the treatment of mastitis by intra-mammary administration.

The compound of the formula may be present in the composition as sole therapeutic agent or it may be present together with other therapeutic agents such as a penicillin or cephalosporin. Considerable advantages accrue from the inclusion of a penicillin or cephalosporin since the resulting composition shows enhanced effectiveness (synergy).

Suitable penicillins for inclusion in the compositions of this invention include benzylpenicillin, phenoxymethylpenicillin, carbenicillin, azidocillin, propicillin, ampicillin, amoxycillin, epicillin, ticarcillin, cyclacillin, pirbenicillin, azlocillin, mezlocillin, celbenicillin, and other known penicillins including pro-drugs therefore such as their in-vivo hydrolysable esters such as the acetoxymethyl, pivaloyloxymethyl, α-ethoxycarbonyloxyethyl or phthalidyl esters of ampicillin, benzylpenicillin or amoxycillin, and aldehyde or ketone adducts of penicillins containing an 6-α-aminoacetamide side chain (such as hetacillin, metampicillin and analogous derivatives of amoxycillin) or α-esters of carbenicillin or ticarcillin such as their phenyl or indanyl α-esters.

Suitable cephalosporins for inclusion in the compositions of this invention include cefatrizine, cephaloridine, cephalothin, cefazolin, cephalexin, cephacetrile, cephamandole nafate, cephapirin, cephradine, 4-hydroxycephalexin, cefaparole, cephaloglycin, and other known cephalosporins or pro-drugs thereof.

Such compounds are frequently used in the form of a salt or hydrate of the like.

Naturally if the penicillin or cephalosporin present in the composition is not suitable for oral administration then the composition will be adapted for parenteral administration. As previously indicated such injectable or infusable compositions are preferred.

Highly favoured penicillins for use in the compositions of this invention include ampicillin, amoxycillin, carbenicillin and ticarcillin. Such penicillins may be used as a pharmaceutically acceptable salt such as the sodium salt. Alternatively the ampicillin or amoxycillin may be used in the form of fine particles of the zwitterionic form (generally as ampicillin trihydrate or amoxycillin trihydrate) for use in an injectable suspension, for example, in the manner hereinbefore described for a compound of this invention.

The preferred penicillin for use in the synergistic composition is amoxycillin, for example as its sodium salt or trihydrate.

Particularly suitable cephalosporins for use in the compositions of this invention include cephaloridine and cefazolin. Such cephalosporins may be used as a pharmaceutically acceptable salt, for example the sodium salt.

When present together with a cephalosporin or penicillin, the ratio of a compound of the invention to the penicillin or cephalosporin agent may vary over a wide range of ratios, such as from 10:1 to 1:10 for example about 3:1, 2:1, 1:1, 1:2, 1:3, 1:4, 1:5 or 1:6, (wt/wt, based on pure free antibiotic equivalent). Orally administrable compositions containing a compound of the invention will normally contain relatively more synergist than corresponding injectable compositions, for example the ratio in an oral composition may be from about 3:1 to about 1:1 whereas a corresponding injectable composition may contain a ratio of about 1:1 to about 1:3 (compound of the invention: penicillin or cephalosporin).

The total quantity of a compound of the invention in any unit dosage form will normally be between 25 and 1000 mg and will usually be between 50 and 500 mg, for example about 62.5, 100, 125, 150, 200 or 250 mg.

Compositions of this invention may be used for the treatment of infections of inter alia, the respiratory tract, the urinary tract and soft tissues in humans and mastitis in cattle.

Normally between 50 and 1000 mg of the compounds of the invention will be administered each day a treatment but more usually between 100 and 750 mg of the compounds of the invention will be administered per day, for example as 1–6 doses, more usually as 2, 3 or 4 doses.

The penicillin or cephalosporin in the synergistic composition of this invention will normally be present at approximately the amount a which it is conveniently used which will usually be expected to be from about 62.5 to 1000 mg per dose, more usually about 125, 250 or 500 mg per dose.

One particularly favoured composition of this invention will contain from 150 to 1000 mg of amoxycillin as the trihydrate or sodium salt and from 25 to 500 mg of a compound of this invention.

Most suitably this form of composition will contain a compound of the formula (III)-(VIII).

A further particularly favoured composition of this invention will contain from 150 to 1000 mg of ampicillin or a pro-drug therefor and from 25 to 500 mg of a compound of this invention.

Most suitably this form of composition will contain ampicillin trihydrate, ampicillin anhydrate, sodium ampicillin, hetacillin, pivampicillinhydrochloride, bacampicillin hydrochloride, or talampicillin hydrochloride. Most suitably this form of the composition will contain a compound of he formula (III)-(VIII).

Most suitably the preceding compositions will contain from 200 to 700 mg of the penicillin component. Most suitably the preceding composition will comprise from 50 to 250 mg of a compound of the formula (III)-(VIII) preferably (III) in crystalline form.

Such compositions may be adapted for oral or parenteral use except when containing an in-vivo hydrolysable ester of ampicillin or amoxycillin in which case the compositions will not be adapted for parenteral administration.

Another particularly favoured composition of this invention will contain from 200 to 2000 mg of carbenicillin, ticarcillin or a pro-drug therefor and from 50 to 500 mg of a compound of the invention.

Suitably this form of composition will contain di-sodium carbenicillin. Suitably this form of the composition will contain di-sodium ticarcillin.

More suitably this form of the composition will contain from 75 to 250 mg of a compound of the formula (III)-(VIII) preferably in crystalline form. Such compositions containing di-salts of carbenicillin and ticarcillin will be adapted for parenteral administration.

The present invention also provides a method of treating bacterial infections in humans or domestic mammals which comprises the administration of a composition of this invention.

Commonly the infection treated will be due to a strain of *Staphylococcus aureus, Klebsiella aerogenes, Escherichia coli, Proteus sp.* or the like. The organisms believed to be most readily treated by an antibacterially effective amount of a compound of this invention is *Staphylococcus aureus.* The other organisms named are more readily treated by using a synergistically effective amount of the compound of the invention and a penicillin or cephalosporin. The administration of the two components may take place separately but in general it we prefer to use a composition containing both the synergist and the penicillin or cephalosporin.

The indications for treatment include respiratory tract and urinary tract infections in humans and mastitis in cattle.

The present invention also provides a process for the preparation of a compound of the formula (II) as hereinbefore defined or an ester thereof which process comprises the hydrogenation of a compound of the formula (X):

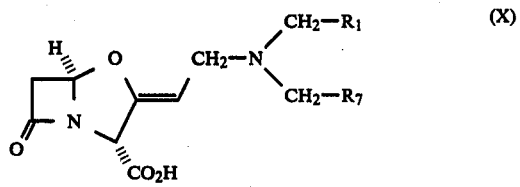

or an ester thereof wherein $R_1$ is as defined in relation to formula (II) and $R_7$ is a group of the sub-formula (a) as defined in relation to formula (II); and thereafter if desired esterifying the zwitterion of the formula (IIa) as hereinbefore defined which was produced by the hydrogenation of the compound of the formula (X) or a hydrogenolysable ester thereof.

When used herein the term "hydrogenolysable ester" means an ester which on hydrogenation is cleaved to yield the parent carboxylic acid.

The hydrogenation is normally carried out in the presence of a transition metal catalyst.

The catalyst we have preferred to use is palladium, for example in the form of palladium on carbon (charcoal), palladium on barium sulphate, palladium on calcium carbonate or the like.

A favoured catayIst is palladium on carbon (sometimes referred to as palladium on charcoal); for example 5%, 10%, 20% or 30% palladium on carbon. The higher palladium content catalyst are particularly apt as smaller total weights of catalyst can be employed thereby avoiding possible problems associated with absorption of product onto the carbon.

A low, medium or high pressure of hydrogen may be used in this reaction, for example from 1 to 6 atmospheres. In general if the catalyst used contains a lower percentage of palladium (for example 5% or 10% palladium) then better yields of the desired product are obtained using a pressure of about 3 to 5 atmospheres of hydrogen, for example about 4 atmospheres of hydrogen. In general if the catalyst used contains a higher percentage of palladium (for example 20% or 30% palladium) then acceptable yields of the desired product may also be obtained at low and medium pressures of hydrogen, for example about 1 to 2 atmospheres of hydrogen. We have found it convenient to use an atmospheric or slightly superatmospheric pressure of hydrogen in conjunction with higher palladium content catalysts.

The reaction is normally carried out at a non-extreme temperature, for example from 0° C. to 30° C. and more usually from 12° C. to 25° C. It is generally convenient to carry out the reaction at ambient temperature.

Suitable solvents for carrying out the hydrogenation include ethanol, n-propanol, isopropanol, tetrahydrofuran, dioxane, ethyl acetate or mixtures of such solvents or such solvents in the presence of water. A favoured solvent is aqueous tetrahydrofuran. A further favoured solvent is a mixture of isopropanol, tetrahydrofuran and water.

Suitably $R_1$ is as group of the sub-formula (b) as hereinbefore defined.

When $R_1$ is a substituted phenyl group then $R_7$ is more suitably a similarly substituted phenyl group or is a phenyl group.

Most suitably $R_7$ is a phenyl group.

Most suitably $R_1$ is a phenyl or substituted phenyl group as shown in and defined as in relation to any of formulae (III)–(VII).

We have preferred to carry out the hydrogenation reaction on a hydrogenolysable ester of a compound of the formula (X) so that a compound of the formula (II) per se is formed by the hydrogenation. Such hydrogenation reactions proceeds at least in part via the formation of a compound of the formula (X). Favoured hydrogenolysable esters include benzyl and substituted benzyl esters such as methoxybenzyl, nitrobenzyl (for example the p-nitrobenzyl ester), chlorobenzyl, bromobenzyl and like esters. A particularly suitable hydrogenolysable ester is the benzyl esters. A further particularly suitable hydrogenolysable ester is the p-methoxybenzyl ester.

The product may generally be isolated from the reaction mixture by filtering off the solids (the catalyst, which should be well washed to remove the product) and then evaporating the solvent, preferably under low pressure, to yield the initial product. Further purification may be effected by such conventional methods as chromatography over cellulose or other mild stationary phase eluting with a $C_{1-4}$ alkanol optionally in the presence of water and optionally in the presence of tetrahydrofuran. Evaporation of the combined active fraction (identified by aqueous potassium permanganate spray on tlc) then yields the desired compound in pure form. The desired product is normally obtained in crystalline form (unless it is an unsalted ester). Trituration under ethanol, isopropanol or the like $C_{1-4}$ alkanol or other conventional solvent such as a ketone, ether or ester solvent or other conventional solvent (for example of up to 6 carbon atoms and more suitably of up to 4 carbon atoms) may also be used to aid crystallisation. Recrystallisation from ethanol or the like may also be employed. The solvent used in such processes may advantageously be moist.

Zwitterionic compounds, such as those of the formulae (III)–(IV) may be obtained from higher yielding reactions by the addition of an $C_{1-4}$ alkanol such as cold ethanol or the like to the initial product.

The initial product of the lower yielding reactions may contain considerably inpurities so that it may be advantageous to wash the initial product by dissolving in a water immiscible organic solvent and extracting into water. Evaporation of the aqueous phase, preferably under a good vacuum, then yields a purer product which may be further purified if desired as previously described.

Unsalted esters of the compounds of the formula (II) tend to be oils so that it is often more convenient for handling to convert them into solid acid addition salts, for example by reaction with one equivalent of an acid. Alternatively the non-hydrogenolysable ester of the compound of the formula (X) may be hydrogenated in the presence of one equivalent of an acid, that is they may be hydrogenated in the form of their acid addition salt.

The compounds of the formula (II) may be hydrogenated in the form of their acid addition salts with a strong acid but this is not a preferred form of the process of this invention.

The present invention also provides a process for the preparation of an ester of a compound of the formula (II) which process comprises the reaction of the compound of the formula (II) with an esterifying agent.

The zwitterionic compound of the formula (II) may be dissolved or suspended in a solvent such as dimethylformamide, hexamethylphosphoramide, dichloromethane, ethyl acetate or other non-esterifiable solvents and therein esterified. Suitable temperatures for such a reaction range from about 0° to about 25° C. Suitable esterifying reagents include reactive halides and their equivalents, alkyl oxonium salts and the like.

When a reagent such as a reactive iodide, chloride, bromide, tosylate, mesylate or the equivalent is used, the resulting salt is generally suitable for use in a composition of this invention. Alternatively, the salt may be converted to a free base or alternative salt. When an alkyl oxonium salt is used, it is preferred to convert the resulting tetrafluoroborate to the free base or alternative salt. The various aforementioned salts may be converted to the free base by neutralisation, for example by contacting a solution of the salt in water with an organic phase, neutralising the salt by adding a base and extracting the liberated amine into the organic phase. This amine may thereafter be re-salted by reacting with an appropriate acid, for example in a dry organic solvent. It is generally preferred to use not more than one equivalent of acid for this process. Alternatively, the originally formed salt may be converted into the alternative salt using an ion exchange material, for example, by passing an aqueous solution of one salt through a bed of an anion exchange resin in the form of the desired salt such as the chloride form.

The salts may normally be obtained in solid form by dissolving in a fairly polar organic solvent (such as ethanol, tetrahydrofuran or the like) and then precipitating using a non-polar solvent such as diethyl ether, cyclohexane or the like.

The salts of the esters of the compounds of the formula (II) may normally be obtained in crystalline form by conventional methods such as trituration under (or crystallisation or recrystallisation from) a suitable organic solvent such as ether, acetone, acetonitrile, tetrahydrofuran of the like.

The present invention also provides a process for the preparation of an ester of the compound of the formula (II) which process comprises the reaction of an acid addition salt of the compound of the formula (II) with an alcohol in the presence of a condensation promoting agent.

Suitable condensation promoting agents for use in this process include carbodiimides such as dicyclohexylcarbodiimide and the chemical equivalents thereof.

The acid addition salt may be formed in situ or may be preformed. The acid employed will normally be a strong acid such as a methane sulphonic acid, p-toluene sulphonic or the like or trifluoroacetic acid or the like.

The reaction is normally carried out in an inert organic solvent. When the ester being formed is that of a liquid alcohol it is convenient to use that alcohol as the solvent or as part of the solvent system. The esterification is generally performed at a non-extreme temperature such as 0° to 35° C., for example from about 10° to 25° C. Conveniently the reaction mixture may be performed at ambient temperature.

The present invention also provides a process for the preparation of an ester of a compound of the formula (II) which process comprises the hydrogenation of a corrosponding ester of a compound of the formula (XI):

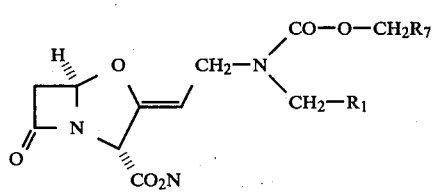
(XI)

wherein $R_1$ is as defined in relation to formula (II) and $R_7$ is as defined in relation to formula (X).

Most suitably $R_7$ is a phenyl group.

The ester of the compound of the formula (XI) is suitably an ester as defined in relation to formula (VIII) or less preferably as defined in relation to formula (IX).

Particularly suitable esters of the compound of the formula (XI) include $C_{1-4}$ alkyl esters especially the methyl and ethyl esters.

The hydrogenation may be performed under the same general conditions as hereinbefore described in relation to the hydrogenation of a compound of the formula (X).

A favoured solvent is tetrahydrofuran optionally in admixture with water or a $C_{1-4}$ alcohol such as ethanol. Conveniently the reaction uses an atmospheric pressure of hydrogen at an ambient temperature.

The present invention also provides a process for the perparation of an ester of a compound of the formula (XI) which process comprises the esterification of the compound of the formula (XI) of a salt thereof.

Most suitably this esterification is effected by the reaction of a salt of a compound of the formula (XI) with a reactive halide or the chemical equivalent thereof.

Suitable salts of the compound of the formula (XI) include the lithium, sodium, potassium and like salts. Suitable esterifying agent include reactive chlorides, bromides, iodides, acid anhydrides, tosylates, mesylates and the like.

The esterification may be effected in a conventional organic solvent such as acetone, dimethylformamide or the like. The reaction is normally effected at a non-extreme temperature such as 0° to 35° C. for example 10° to 25° C. Conveniently the reaction is performed at ambient temperature.

The acid of the formula (XI) may also be esterified by reacting with an alcohol in the presence of a condensation promoting reagent such as a carbodiimide, for example dicyclohexylcarbodiimide, or the chemical equivalent thereof. Such reactions may be carried out under conditions similar to those hereinbefore described for the same type of reaction carried out on an acid addition salt of a compound of the formula (II).

The present invention also provides a process for the preparation of a compound of the formula (XI) or a salt thereof which process comprises the reaction of a compound of the formula (II), or a salt thereof, as hereinbefore defined with a compound of the formula (XII):

$$Y\text{-CO-O-}R_7 \qquad (XII)$$

wherein $R_7$ is as defined in relation to formula (X) and Y is a readily displaceable group to form a compound of the formula (XI).

Favoured groups Y include the chlorine atom and chemically equivalent atoms or groups such as the bromine atom or a $OR_7$ group or the like.

A preferred compound of the formula (XII) is benzylchloroformate.

The reaction may be performed under conventional acylation conditions, for example in non-acylatable organic solvent such as acetone in the presence of an acid acceptor such as lithium bicarbonate, sodium carbonate, potassium carbonate or the like at a non-extreme temperature such as 10° to 30° C., for example at about 0° to 10° C.

We have found it convenient to carry out the acylation on a salt of the compound of the formula (II) such as an alkali metal salt and in particular the lithium salt.

From the preceding descriptions it will be realised that from a broad process aspect the present invention provides a process for the preparation of a compound of the formula (II) as hereinbefore defined or an ester thereof which process comprises the hydrogenation of a compound of the formula (X) as hereinbefore defined or an ester thereof; and thereafter if desired esterifying the zwitterion of the formula (IIa) as hereinbefore defined which was produced by the hydrogenation of the compound of the formula (X) or a hydrogenolysable ester thereof; or thereafter if desired acylating the zwitterion of the formula (IIa) as hereinbefore defined which was produced by the hydrogenation of the compound of the formula (X) with a compound of the formula (XII) as hereinbefore defined to form a compound of the formula (XI) as hereinbefore defined and thereafter esterifying the resulting compound of the formula (XI) as a salt thereof and subjecting the thus formed ester to hydrogenation to yield the desired ester of a compound of the formula (II).

Since the compounds of the formula (XI) and the salts and ester thereof are as use as intermediates they form part of this invention. Suitably the compounds of the formula (XI) are in the form of an ester of a type hereinbefore described. Suitably the compounds of the formula (XI) are in the form of a salt such as in alkali metal salt, for example the lithium salt.

The intermediates of the formula (X) and their esters may be prepared by the methods of Belgian No. 847044 or U.S. Ser. No. 731,928.

We have chosen to name the novel compounds of this invention as notional derivatives of deoxyclavular is of the formula (XIII):

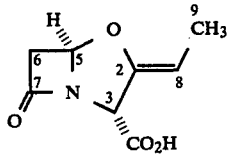

(XIII)

Thus on this system the amino-substituent is defined as being attached to the 9-carbon atom.

The processes of this invention may be adapted to the preparation of the following compounds:
9-N-Benzylaminodeoxyclavulanic acid
9-N-(2-Methoxybenzyl)aminodeoxyclavulanic acid
9-N-(3-Methoxybenzyl)aminodeoxyclavulanic acid
9-N-(4-Methoxybenzyl)aminodeoxyclavulanic acid
9-N-(4-Hydroxybenzyl)aminodeoxyclavulanic acid
9-N-(3-Hydroxybenzyl)aminodeoxyclavulanic acid
9-N-(4-Hydroxy-3-methoxybenzyl)aminodeoxyclavulanic acid
9-N-(3-Hydroxy-4-methoxybenzyl)aminodeoxyclavulanic acid
9-N-(2-Fluorobenzyl)aminodeoxyclavulanic acid
9-N-(3-Fluorobenzyl)aminodeoxyclavulanic acid
9-N-(4-Fluorobenzyl)aminodeoxyclavulanic acid
9-N-(2-Methylbenzyl)aminodeoxyclavulanic acid
9-N-(3-Methylbenzyl)aminodeoxyclavulanic acid
9-N-(4-Methylbenzyl)aminodeoxyclavulanic acid
9-N-(2-Acetamidobenzyl)aminodeoxyclavulanic acid
9-N-(3-Acetamidobenzyl)aminodeoxyclavulanic acid
9-N-(4-Acetamidobenzyl)aminodeoxyclavulanic acid
9-N-(4-Propionamidobenzyl)aminodeoxyclavulanic acid
9-N-(4-Chlorobenzyl)aminodeoxyclavulanic acid
9-N-(2-Hydroxyethyl)aminodeoxyclavulanic acid
9-N-Ethylaminodeoxyclavulanic acid
9-N-(2-Hydroxypropyl)aminodeoxyclavulanic acid
9-N-Propylaminodeoxyclavulanic acid The present invention also provides esters of the preceding compounds which esters may be in the form of acid addition salts. Suitable esters include:
methyl
ethyl
methoxymethyl
benzoylmethyl
acetylmethyl
benzyl
4-methoxybenzyl
2-hydroxyethyl
carboxymethyl Suitable acid addition salts are normally and preferably those with pharmaceutically acceptable acids.

The following Descriptions illustrate the processes used to prepare intermediates. The secondary amines used to displace acyloxyl groups from the acylated clavulanic acid derivatives may be prepared by the hydrogenation of a Schiffs base prepared by the reaction of an aldehyde and primary amine in conventional manner. The following Demonstrations illustrate the activities of the compounds of this invention. The following Examples illustrate the invention.

DESCRIPTION 1

Benzyl 9-(N-benzyl-N-2-hydroxyethyl)aminodeoxyclavulanate

Clavudiene benzyl ester (0.5 g) in acetonitrile (10 ml) was cooled to 0° C., N-benzyl-2-hydroxyethylamine (0.36 g) was added and the reaction mixture stirred for 2½ hours. Ethyl acetate (100ml) was added and the mixture evaporated to low volume. The residue was subjected to column chromatography using ethyl acetate as eluent. The product, isolated in low yield, has an ir spectrum (liquid film) as follows: 3400 (Broad, —OH), 1800 (β-lactam C=O), 1740 (ester C=O), 1700 (C=C), 1695cm$^{-1}$ (aromatic protons).

DESCRIPTION 2 p-Methoxybenzyl 9-(N-benzyl-N-2-hydroxyethyl)amino-deoxyclavulanate p-Methoxybenzyl trichloroacetylclavulanate (5.37 mM) in dry dimethylformamide (75 cm$^3$) at $-10°$ C. was treated with N-benzyl-N-2-hydroxyethylamine (1.55 cm$^3$) and stirred at this temperature for 5 hours. The mixture was poured into ethyl acetate (150 cm$^3$) and washed with water (3×100 cm$^3$), dried and evaporated to an oil (0.38 g) Rf (SiO$_2$/ethyl acetate:cyclohexane; 1:1)=0.13ν(film) 3400, 1810, 1750, 1620 cm$^{-1}$.

DESCRIPTION 3

Benzyl 9-(N-benzyl-N-ethyl)aminodeoxyclavulanate

Benzyl trichloroacetylclavulanate (9.2 mM) in dry dimethylformamide (30 cm$^3$) at $-60°$ C. was treated with N-benzylethylamine (2.74 cm$^3$) and stirred for 3½ hours at this temperature. The mixture was poured into ethyl acetate (150 cm$^3$) and washed with water (3×100 cm$^3$), dried and evaporated in vacuo to yield an oil (4.43 g). Rf (SiO$_2$/ethyl acetate:cyclohexane; 1:1) 0.3. ν(film) 1804, 1750 cm$^{-1}$.

DESCRIPTION 4

Benzyl 9-(N-benzyl-N-isopropyl)aminodeoxyclavulanate

Clavudiene benzyl ester (0.5 g) in acetonitrile (10 ml) was cooled in ice-water. N-isopropylbenzylamine (0.39 g, 1.3 moles) was added with stirring. The reaction mixture was allowed to warm to room temperature and stirred for 3 hours. Ethyl acetate (100 ml) was added, and the solution evaporated to low bulk in vacuo. The residue was subjected to column chromatography on silica gel using cyclohexane and ethyl acetate as eluents. The product was eluted after the unreacted diene.

DESCRIPTION 5

Benzyl 9-(N,N-dibenzyl)aminodeoxyclavulanate

Benzyl dichloroacetyl-clavulanate (0.8 g) was dissolved in dry dimethylformamide and cooled to 0° C., treated with dibenzylamine (768 μl; 0.004 mol) in dry dimethylformamide (4 ml) over 15 minutes, the temperature being maintained at 0° C. The resulting yellow solution was stirred at 0° for 2½ hours and at room temperature for 4 hours. Ethylacetate was added (100 ml) and the solution washed with water (3×25 ml), dried and evaporated. The oil was purified by fast gradient elution on silica gel using ethyl acetate/cyclohexane as the eluting solvent (Yield 0.33 g). Rf (SiO$_2$/ethylacetate:cyclohexane; 1:1) =0.76. ν(film) 1810, 1755, 1700; δ(CDCl$_3$) 2.80 (1H, d, J 16 Hz, 6β-C$\underline{H}$) 3.05 (2H, d, J 7 Hz, 9-C$\underline{H}_2$), 3.17-3.37 (1H, m, 6α-C$\underline{H}$) 3.32 (4H, s, 2×NC$\underline{H}_2$C$_6$H$_5$), 4.59 (1H, t, J 7 Hz, 8-C$\underline{H}$), 4.90 (1H, s, 3-C$\underline{H}$), 5.03 (2H, s, OC$\underline{H}_2$C$_6$H$_5$) 5.57 (1H, d, J 3 Hz, 5α-C$\underline{H}$), 7.20 (15H, s, 3×C$_6$$\underline{H}_5$).

DESCRIPTION 6

Benzyl 9-(N,N-dibenzyl)aminodeoxyclavulanate

Clavudiene benzyl ester (271 mg) in dry acetonitrile (4 ml) at 0° C. was treated with dibenzylamine (197 mg) in dry acetonitrile (2 ml) over 5 minutes. The reaction mixture was stirred at 0° C. for 2 hours and at room temperature for 2 hours. The solvent was removed by evaporation and the residue dissolved in ethyl acetate, washed with water, dried, evaporated and fractionated on silica-gel to yield the desired product which was purified by chromatography.

DESCRIPTION 7

Benzyl 9-[N-benzyl-N-(dl-2-hydroxypropyl)]aminodeoxyclavulanate

Benzyl dichloroacetylclavulanate (0.8 g) in dry dimethylformamide (20 ml) was cooled to 0° C. and a solution of dl-1-benzylamino-propan-2-ol (0.65 g) in dry dimethylformamide was added slowly. Stirring was continued for 4 hours at 0° C. A more polar component was formed (thin layer chromatograph) and worked up as described in description 5 and chromatographed to give the desired product (0.16 g).

DESCRIPTION 8

Benzyl 9-[N-benzyl-N-(dl-2-hydroxypropyl)]aminodeoxyclavulanate

Benzyl trichloroacetylclavulanate (2.5 g; 5.8 mm) in dry dimethyl-formamide (50 cm$^3$) at −10° was treated with N-benzyl-N-(dl-2-hydroxypropyl)amine (1.9 equivalents) in dimethylformamide (20 cm$^3$) dropwise. The reaction mixture was stirred at −10° for 4½ hours, poured onto cold (0°) ethylacetate and the organic layer washed with water (5×75 cm$^3$). After drying, the ethyl acetate solution was passed through a ½ cm ×2½ cm dia. column of silica gel eluting with ethyl acetate (75 cm$^3$) until the eluate was no longer coloured. The ethyl acetate solution was extracted with dilute acetic acid (3×50 cm$^3$), the aqueous extracts were combined and treated with sodium bicarbonate in the presence of fresh ethyl acetate (80 cm$^3$) with vigorous stirring until the pH of the aqueous phase was 8. The ethyl acetate phase was dried and evaporated in vacuo to yield product as a yellow oil (700 mg); R f (SiO$_2$/ethylacetate:cyclohexane; 1:1)=0.28, detection by aqueous potassium permanganate spray; $\nu_{max}$ (KBr) 3410 (broad), 1795, 1740, 1700 cm$^{-1}$;δ[(CD$_3$)$_2$CO] 0.98 (3H, d, J 6 Hz, CHC$\underline{H}_3$), 2.28, 2.30 (2H, 2×d, J 6 Hz, NC$\underline{H}_2$-CH(OH)), 2.91, 2.94 (1H, 2×d, J 17 Hz, 6β-C$\underline{H}$), 3.15 (2H, d, J 7 Hz, 9-C$\underline{H}_2$), 3.2-3.9 (5H, m, NC$\underline{H}_2$C$_6$H$_5$, —CH$_2$C-$\underline{H}$(OH)CH$_3$, 6α-C$\underline{H}$, CHO$\underline{H}$), 4.72 (1H, t, J 7 Hz, 8-C$\underline{H}$), 5.06 (1H, s, 3-C$\underline{H}$).

DESCRIPTION 9

Benzyl 9-N-benzyl-N-(4-methoxybenzyl)aminodeoxyclavulanate

Benzyl dichloroacetylclavulanate (4.8 g; 12 mM) in dimethylformamide (50 ml) at 0° was treated with N-benzyl-N-4-methoxybenzylamine (5.2 g; 1.9 equivalents) dropwise. The reaction mixture was stirred at 0° for 1 hour and then at 20° for 5 hours. The reaction mixture was then poured into cold (0°) ethyl acetate and the organic layer washed with water (3×75 ml) and saturated brine (5×75 ml). The ethyl acetate phase was dried and evaporated in vacuo to yield 6.6 g of a coloured oil. This oil was chromatographed on silica gel, eluting with ethyl acetate - cyclohexane; 1:1. Fractions containing the title compound were collected and evaporated in vacuo to yield benzyl 9-[N-benzyl-N-(4-methoxybenzyl)amino] deoxyclavulanate (2.24 g) as a colourless oil. Rf (SiO$_2$/ethyl acetate: cyclohexane; 1:1)=0.70.

ν(film) 1805, 1750, 1690, 1610, 1510, 1300, 1250, 1175, 740, 700 cm$^{-1}$.

δ(CDCl$_3$) 2.87 (1H, d, J 17Hz, 6βC$\underline{H}$), 3.10 (2H, d, J 7Hz, 9C$\underline{H}_2$), 3.33 (1H, dd, J 17 Hz and 3Hz, 6αC$\underline{H}$), 3.38, 3.43 (4H, 2×s, NC$\underline{H}_2$C$_6$H$_5$ and NC$\underline{H}_2$C$_6$H$_4$OCH$_3$), 3.70 (3H, s, OC$\underline{H}_3$), 4.71 (1H, t, J 7 Hz, 8C$\underline{H}$), 5.00 (1H, s, 3C$\underline{H}$), 5.10 (2H, s, OC$\underline{H}_2$C$_6$H$_5$), 5.51 (1H, d, J 3 Hz, 5αC$\underline{H}$), 6.75 (2H, d, J 8 Hz, aromatic, ortho to methoxyl), 7.09-7.20 (12H, m, aromatic meta to methoxyl and 2×C$_6\underline{H}_5$).

DESCRIPTION 10

Benzyl 9-[N-benzyl-N-(4-fluorobenzyl)]aminodeoxyclavulanate

Benzyl dichloroacetylclavulanate (8.5 g; 21 mM) in dimethylformamide (75 cm$^3$) at 0° was treated dropwise with N-benzyl-N-4-fluorobenzylamine (8.1 g; 1.9 equivalents). The reaction mixture was stirred at 0° for 1 hour and 5 hours at 20°. The reaction mixture was poured into cold (0°) ethyl acetate (150 cm$^3$) and the organic layer was then washed with water (3×75 cm$^3$) and saturated brine (4×75 cm$^3$). The ethyl acetate phase was dried and evaporated in vacuo to yield 10 g of a coloured oil. 3 g of this crude product was chromatographed on silica gel, eluting with ethyl acetate—cyclohexane; 1:1. Fractions containing the title compound were collected and evaporated in vacuo to yield benzyl 9-[N-benzyl-N-(4fluorobenzyl)] aminodeoxyclavulanate (1 g) as a colourless oil. Rf (SiO$_2$/ethyl acetate: cyclohexane; 1:1)=0.70, detection by potassium permanganate spray.

ν(film) 1805, 1750, 1690, 1508, 1305, 1220, 820, 740, 700 cm$^{-1}$.

δ(CDCl$_3$) 2.90 (1H, d, J 17 Hz, 6βC$\underline{H}$), 3.09 (2H, d, J 7 Hz, 9CH$_2$), 3.38 (1H, dd, J 17 Hz and 3 Hz, 6αC$\underline{H}$), 3.39, 3.42 (4H, 2×s, NC$\underline{H}_2$—C$_6$H$_5$ and NC$\underline{H}_2$C$_6$H$_4$F), 4.70 (1H, t, J 7 Hz, 8C$\underline{H}$), 5.02 (1H, s, 3-C$\underline{H}$), 5.12 (2H, s, OC$\underline{H}_2$C$_6$H$_5$), 5.54 (1H, d, J 3 Hz, 5αC$\underline{H}$), 6.80- 7.25 (14H, m, 2×CH$_2$C$_6$H$_5$, and CH$_2$C$_6$H$_4$F).

DESCRIPTION 11

Benzyl 9-[N-benzyl-N-(4-methylbenzyl)]aminodeoxyclavulanate

Benzyl dichloroacetylclavulanate (8.5 g; 21 mM) in dimethylformamide (75 cm$^3$) at 0° was treated with N-benzyl-N-(4-methylbenzyl)amine (8.40 g; 1.9 equivalents), dropwise and then stirred for 1 hour at 0° and 3 hours at 20°. The reaction mixture was poured into cold (0°) ethyl acetate (150 cm$^3$) and the organic phase washed with water (3×75 cm$^3$) and saturated brine (4×75 cm$^3$). The ethyl acetate phase was dried and evaporated in vacuo to yield 11 g of a coloured oil. 1 g of this crude product was chromatographed on silica gel, eluting with ethyl acetate:cyclohexane; 1:1. Fractions containing the title compound were collected and were evaporated in vacuo to yield 250 mg (25%) of a colourless oil; Rf (SiO$_2$/ethyl acetate:cyclohexane; 1:1)=0.70; detection by aqueous potassium permanganate spray.

Further fractions containing the title compound in approximately 80% purity were collected, yield=0.6 g.

$\nu$(film) of purest product: 1805, 1750, 1690, 1510, 1495, 1450, 1300, 1230, 1175, 1120, 1080, 1040, 1020, 965, 890, 800, 740, 700 cm$^{-1}$.

$\delta$(CDCl$_3$) 2.28 (3H, s, —C$_6$H$_4$CH$_3$), 2.88 (1H, d, J 17 Hz, 6$\beta$CH), 3.10 (2H, d, J 7 Hz, 9CH$_2$), 3.35 (1H, dd, J 17 Hz and 3 Hz, 6$\alpha$CH), 3.42 (4H, s, NCH$_2$C$_6$H$_5$ and NCH$_2$C$_6$H$_4$CH$_3$), 4.71 (1H, t, J 7 Hz, 8CH), 5.00 (1H, s, 3CH), 5.10 (2H, s, OCH$_2$C$_6$H$_5$), 5.52 (1H, d, J 3Hz, 5$\alpha$CH), 6.95-7.27 (14H, m, 2×CH$_2$C$_6$H$_5$ and CH$_2$C$_6$H$_4$CH$_3$).

DESCRIPTION 12

Benzyl 9-[N-benzyl-N(4-benzoxy-3-methoxybenzyl)benzyl-]aminodeoxyclavulanate.

Benzyl dichloroacetyl-clavulanate (1.9 g; 4.7 mM) in dry dimethylformamide (50 cm$^3$) at 0° C. was treated with N-benzyl-N-(4-benzoxy-3-methoxybenzyl)amine (3 g; 1.9 equivalents) dropwise. The reaction mixture was stirred at 0° C. for 1 hour then at 20° C. for 5 hours. The reaction mixture was then poured into cold (0°) ethyl acetate and the organic layer washed with water (3×75 cm$^3$) and saturated brine (5×75 cm$^3$). The ethyl acetate phase was dried and evaporated in vacuo to yield a coloured oil. This oil was chromatographed on silica gel, eluting with ethyl acetate - cyclohexane; 1:1. Fractions were collected containing the title compound; these were evaporated in vacuo to yield benzyl 9-[N-benzyl-N-(4-benzoxy-3-methoxybenzyl)] aminodeoxyclavulanate (0.1 g) as a colourless oil.

Rf (SiO$_2$/ethyl acetate:cyclohexane; 1:1)=0.70.

$\nu$(film) 1800, 1750, 1675, 1590, 1510, 1450, 1380, 1300, 1260, 1225, 1160, 1140, 1080, 1015, 805, 740, 700 cm$^{-1}$.

$\delta$(CDCl$_3$) 2.90 (1H, d, J 17 Hz, 6$\beta$CH), 3.03 (2H, d, J 7 Hz, 9CH$_2$), 3.37 (1H, dd, J 17 and 3 Hz, 6$\alpha$CH), 3.37, 3.42 (6H, 2×s, NCH$_2$C$_6$H$_5$ and NCH$_2$C$_6$H$_3$ OCH$_3$, OCH$_2$C$_6$H$_5$), 3.80 (3H, s, OCH$_3$), 4.72 (1H, t, J 7 Hz, 8CH), 5.01 (1H, s, 3CH), 5.54 (1H, d, J 3 Hz, 5$\alpha$CH), 6.70 -7.34 (18H, m, 3×CH$_2$C$_6$H$_5$ and 2 protons ortho to the CH$_2$ of CH$_2$(C$_6$H$_3$)(OCH$_3$)OCH$_2$C$_6$H$_5$.

DESCRIPTION 13

Benzyl 9-[N-(4-benzyloxybenzyl)-N-benzyl]aminodeoxyclavulanate

Benzyl dichloroacetylclavulanate (7.2 g; 18 mm), in dry dimethylformamide (75 cm$^3$) at 0° was treated with N-(4-benzoxybenzyl)-N-benzylamine (1.9 equivalents) and stirred at 0° for 3 hours, then poured into ethyl acetate (150 cm$^3$) and washed with water (5×50 cm$^3$) and brine (3×50 cm$^3$), dried (anhydrous magnesium sulphate) and evaporated in vacuo to yield a coloured oil. This oil was chromatographed on silica eluting with ethylacetate/cyclohexane; 1:1. Fractions were collected containing the title compound (detection by aqueous potassium permanganate spray), RF (SiO$_2$ ethylacetate/cyclohexane; 1:1)=0.81. Combined fractions were evaporated to an oil, yield of approximately 70% pure material=2.7 g, pure fractions were collected for spectroscopy. $\nu$(film) 1800, 1745, 1690, 1600, 1595, 1510, 1450, 1380, 1300, 1230, 1170, 1129, 1080, 1045, 1020, 830, 740, 700 cm$^{-1}$; $\delta$(CDCl$_3$) 2.87 (1H, d, J 17 Hz, 6$\beta$CH), 3.09 (2H, d, J 7 Hz 9CH$_2$), 3.33 (2H, dd, J 17 Hz and 3 Hz, 6$\alpha$CH), 3.37, 3.42 (4H, 2×s, NCH$_2$C$_6$H$_5$ and NCH$_2$C$_6$H$_4$OCH$_2$C$_6$H$_5$), 4.70 (1H, t, J 7 Hz, 8CH), 4.97 (3H, broad S, C$_6$H$_4$OCH$_2$C$_6$H$_5$ and 3CH), 5.10 (2H, S, CO$_2$CH$_2$C$_6$H$_5$), 5.51 (1H, d, J, 3 Hz, 5$\alpha$-CH), 6.80 (2H, d, J 9 Hz aromatic protons ortho to benzyloxy), 7.0 -7.30 (17H, m, N-CH$_2$C$_6$H$_5$, OCH$_2$C$_6$H$_5$, CO$_2$CH$_2$C$_6$H$_5$, aromatic protons meta to benzyloxy).

DESCRIPTION 14

Benzyl 9-[(N-3,4-dimethoxybenzyl)-N-benzylamino]deoxyclavulanate

Benzyl dichloroacetylclavulanate (6.56 g; 16 mm) in dry dimethylformamide (50 cm$^3$) at 0° was treated with N-(3,4-dimethoxybenzyl)-N-benzylamine (8 g; 1.9 equivalents) in 30 cm$^3$ dimethylformamide and stirred for 2 hours at 0° then 2 hours at 10°. Then poured into cold ethyl acetate (150 cm$^{3l}$) and washed with water (5×50 cm$^3$) and saturated brine (5×50 cm$^3$), dried (anhydrous magnesium sulphate) and evaporated in vacuo to yield an oil; 10.1 g. 1.2 g of this crude product was chromatographed on silica gel eluting with ethylacetate/cyclohexane; 1:1. Fractions were collected containing the title compound.

Rf=0.74 (SiO$_2$/ethylacetate: cyclohexane; 1:1), detection by aqueous potassium permanganate spray. Combined fractions were evaporated in vacuo to yield an oil; 0.35 g. $\nu$(film) 1804, 1750, 1690, 1510, 1480, 1305, 1260, 1235, 1175, 1155, 1145, 1120, 1030, 1015, 807, 740, 700 cm$^{-1}$.

$\delta$(CDCl$_3$) 2.91 (1H, d, J 17 Hz, $\beta$CH), 3.12 (2H, d, J 7 Hz, 9CH$_2$), 3.38 (1H, dd, J 17 Hz and 3 Hz, 6$\alpha$-CH), 3.39, 3.43 (4H, 2×s, 2×NCH$_2$), 3.83 (6H, S, 2×OCH$_3$), 4.73 (1H, dt, J 7 Hz and <1 Hz, 8CH), 5.01 (1H, d, J <1 Hz, 3CH), 5.12 (2H, S, OCH$_2$C$_6$H$_5$), 5.55 (1H, d, J 3 Hz, 5$\alpha$-CH), 6.73 -6.83 (3H, m, aromatic protons ortho to CH$_2$), 7.23 (10H, m, 2×C$_6$H$_5$).

DESCRIPTION 15

Benzyl 9-[N-(4-acetylaminobenzyl)-N-benzyl]aminodeoxyclavulanate

Benzyl dichloroacetylclavulanate (4.4 g; 11 mm) in dry dimethylformamide (50 cm$^3$) at 0° was treated with N-(4-acetamidobenzyl)benzylamine (5.3 g; 1.9 equivalents) dropwise in 20 cm$^3$ dimethylformamide with stirring. Stirring was continued for 4 hours at 0° then poured into ethyl acetate (200 cm$^3$) and washed with water (5×50 cm$^3$) and brine (3×50 cm$^3$), dried (anhydrous magnesium sulphate) and evaporated to a foam. This crude product was chromatographed on silica eluting with ethylacetate-cyclohexane; 1:1 graduating to neat ethylacetate. Fractions were collected containing the title compound (detection by aqueous potassium permanganate spray). Rf (SiO$_2$/ethylacetate-cyclohexane; 1:1)=0.30. Combined fractions were evaporated in vacuo to give a crisp foam, 2.51 g. $\nu$(Nujol Mull) 3300, 1800, 1745, 1690, 1665, 1600, 1530, 1510, 1450, 1410, 1370, 1310, 1260, 1170, 1120, 1040, 1015, 740, 700 cm$^{-1}$.

$\delta$(CDCl$_3$) 2.10 (1H, S, CH$_3$CONH), 2.91 (1H, d, J 17 Hz, 6$\beta$CH), 3.10 (2H, d, J 7 Hz, 9CH$_2$), 3.37 (1H, dd, J 17 and 3 Hz, 6$\alpha$CH), 3.40, 3.43 (4H, 2×s, 2×NCH$_2$), 4.69 (1H, t, J 7 Hz, 8CH), 4.98 (1H, s, 3CH), 5.11 (2H, s, CO$_2$CH$_2$C$_6$H$_5$), 5.33 (1H, d, J 3 Hz, 5$\alpha$CH), 7.12 -7.41 (15H, m, 2×C$_6$H$_5$, CH$_2$C$_6$H$_4$ - p-NHCOCH$_3$, CONH).

DESCRIPTION 16

Benzyl 9-[N-(2-fluorobenzyl)-N-benzyl]aminodeoxyclavulanate

Benzyl dichloroacetylclavulanate (8 g; 0.02M) in dry dimethylformamide (100 cm$^3$) at 0° was treated with N-(2-fluorobenzyl)benzylamine (1.9 equivalents) dropwise in dimethylformamide (30cm$^3$) and stirred for 4 hours at 20° then 2 hours at 20°. The mixture was poured into ethylacetate (200cm$^3$) and washed with water (4×50 cm$^3$) and saturated brine (5×50 cm$^3$) dried (anhydrous magnesium sulphate) and evaporated to an oil, yield=10 g. 2 g of this crude product was chromatographed on silica eluting with ethylacetate/cyclohexane (1:2). Fractions were collected containing the title compound, Rf (SiO$_2$/ethylacetate-cyclohexane; (1:1)=0.78 (detection by aqueous potassium permanganate spray). Combined fractions were evaporated in vacuo to yield an oil, yield=0.4 g. $\nu$(film) 1800, 1745, 1690, 1490, 1450, 1305, 1230, 1180, 1120, 1045, 1020, 760, 700 cm$^{-1}$. $\delta$(CDCl$_3$) 2.94 (1H, d, J 17 HZ, 6$\beta$CH), 3.13 (2H, d, J 7 HZ, 9CH$_2$), 3.41 (1H, dd, J 17 and 3 HZ, 6$\alpha$CH), 3.50, 355 (4H, b 2×s, 2×NCH$_2$), 4.75 (1H, t, J 7 HZ, 8CH), 5.02 (1H, s, 3CH), 5.14 (2H, s, CO$_2$CH$_2$C$_6$H$_5$), 5.57 (1H, d, J 3 HZ, 5-$\alpha$-CH), 6.94–7.47 (4H, m, CH$_2$C$_6$H$_4$F), 7.24, 7.26 (10H, 2×s, 2×CH$_2$C$_6$H$_5$).

DESCRIPTION 17

Benzyl 9-[N-(2-methoxybenzyl)-N-benzyl]aminodeoxyclavulanate

Benzyl dichloroacetylclavulanate (21 mm) in dry dimethylformamide (70 cm$^3$) at 0° was treated with N-2-methoxybenzyl-N-benzylamine (1.9 equivalents) in dimethylformamide (30 cm$^3$) and stirred for 3½ hours at 0° then 1½ hours at 20°. The mixture was poured into ethylacetate (200 cm$^3$) and washed with water (5×50 cm$^3$) and saturated brine (5×50 cm$^3$), dried (anhydrous magnesium sulphate) and evaporated in vacuo to yield an oil, 13 g. 5 g of this crude product was chromatographed on silica eluting with ethylacetate:cyclohexane (1:1) Fractions were collected containing the title compound, Rf (SiO$_2$: ethyl acetate:cyclohexane; 1:1)=0.74. Combined fractions were evaporated in vacuo to yield an oil, 1.2 g. $\nu$(film) 1805, 1745, 750, 700 cm$^{-1}$. $\delta$(CDCl$_3$) 2.93 (1H, s, J 17 Hz, 6$\beta$CH), 3.17 (2H, d, J 7 Hz, 9CH$_2$), 3.40 (1H, dd, J 17 and 3 Hz, 6 $\alpha$CH), 3.54. 3.57 (4H, 2×s, 2×NCH$_2$), 3.75 (3H, s, OCH$_3$), 4.86 (1H, t, J 7 Hz, 8CH), 5.02 (1H, s, 3CH), 5.14 (2H, s, CO$_2$CH$_2$C$_6$H$_5$), 5.57 (1H, d, J 3 Hz, 5 $\alpha$CH), 6.75–7.45 (14H, m, 2×CH$_2$C$_6$H$_5$, CH$_2$C$_6$H$_4$OCH$_3$).

DESCRIPTION 18

Benzyl trichloroacetylclavulanate

Benzyl clavulanate (5.78 g, 20 mmol) in dry methylene chloride (100 ml) was cooled to −30° C. and treated with pyridine (1.61 ml). Trichloroacetyl chloride (2.23 ml, 20 mmol) in dry methylene chloride (10 ml) was then added dropwise over a period of 10 mins. After a further 10 mins. at −30° C. the reaction mixture was poured into dilute hydrochloric acid (100 ml, 2M). The organic phase was washed with water, sodium bicarbonate solution, brine, dried and evaporated to afford the product as an oil, 7.81 g (90%). $\nu$max (film) 1800, 1750 and 1680 cm$^{-1}$.

DESCRIPTION 19

Benzyl dichlorocetylclavulanate

Benzyl calvulanate (20.2 g; 70 mm) in dichloromethane (100 cm$^3$) was treated with dry pyridine (1 equivalent) and cooled to −20°. Dichloroacetyl chloride (10.3 g; 1 equivalent) was added in dichloromethane (20 cm$^3$), dropwise, and the reaction stirred for 20 minutes. The mixture was washed with water (5×100cm$^3$) and saturated brine (5×100 cm$^3$), dried (anhydrous magnesium sulphate) and evaporated in vacuo to an oil, yield =27.5 g (98%), $\nu$(film) 1800, 1745, 1690, 1295, 1170, 1120, 1085, 1042, 1020, 1000, 955, 890, 815, 742, 700 cm$^{-1}$. $\delta$(CDCl$_3$) 3.05 (1H, d, J 17 Hz, 6$\beta$CH), 3.50 (1H, dd, J17 and 3 Hz, 6$\alpha$CH), 4.82 (3H, s, 8CH and 9CH$_2$), 5.10 (1H, s, 3CH), 5.17 (2H, s, CH$_2$C$_6$H$_5$), 5.70 (1H, d, J 3 Hz, 5$\alpha$ CH), 5.90 (1H, s, CHCl$_2$), 7.32 (5H, s, CH$_2$C$_6$H$_5$).

DESCRIPTION 20

Benzyl monochloroacetylclavulanate

Benzyl clavulanate (2.51 g, 8.7 mmol) was dissolved in methylene chloride (30 ml) and treated with pyridine (0.775 ml, 9.60 mmol) at room temperature. The reaction mixture was cooled to −30° C. and chloroacetyl chloride (0.69 ml, 8.7 mmol) in methylene chloride (10 ml) was added dropwise over ten minutes. After stirring at −30° C. for a further ten minutes the reaction mixture was poured into dilute hydrochloric acid and extracted with methylene chloride. The organic phase was washed successively with dilute hydrochloric acid, sodium bicarbonate solution, brine, and dried (MgSO$_4$). Evaporation in vacuo afforded a pale yellow oil homogeneous by t.l.c., 3.10 g. $\nu$max (CHCl$_3$) 1803, 1755 (br) and 1700 cm$^{-1}$.

DESCRIPTION 21

Methyl dichloroacetylclavulanate

Methyl clavulanate (1.03 g; 4.8 mm) in dichlormethane (30cm$^3$) was treated with pyridine (1 equivalent) and cooled to −20°, then treated with dichloroacetyl chloride (1 equivalent) and stirred for 10 minutes. The solution was washed with water (2×50 cm$^3$) and saturated brine (5×50 cm$^3$), dried (anhydrous magnesium sulphate) and evaporated in vacuo to an oil, 1.31 g.

$\nu$(film) 1805, 1750, 1690, 1300, 1240, 1165, 1045, 1010, 960, 890, 820 cm$^{-1}$. $\delta$(CDCl$_3$) 3.08 (1H, d, J 17 Hz, 6$\beta$CH), 3.51 (1H, dd, J 17 and 3 HZ, 6$\alpha$CH), 3.77 (3H, s, CO$_2$CH$_3$), 4.85 (3H, s, 8CH and 9CH$_2$), 5.08 (1H, s, 3CH), 5.72 (1h, d, J 3 HZ 5 $\alpha$-CH), 5.91 (1H, s, CHCl$_2$).

DESCRIPTION 22

Methyl 9-[N-(4-acetamidobenzyl)-N-benzyl]aminodeoxyclavulanate

Methyl dichloroacetylclavulanate (1.25 g; 3.86 mm) in dimethylfomamide (30 cm$^3$) was treated at 0° with N-(4-acetamidobenzyl) benzylamine (1.9 equivalents) and stirred for 4 hours; poured into ethylacetate (200 cm$^3$) and washed with water (5×50 cm$^3$) and saturated brine (5×50 cm$^3$), dried (anhydrous magnesium sulphate) and evaporated in vacuo to an oil. This oil was chromatographed on silica eluting with ethylacetate-cyclohexane 1:1 grading to neat ethylacetate; fractions were collected containing the title compound, Rf (SiO$_2$/ethylacetate)=0.60. Combined fractions fractions were evaporated in vacuo to yield an oil, yield=0.61 g. $\nu$(film) 3300 (broad), 1800, 1750, 1690, 1670, 750, 700 cm$^{-1}$. $\nu$(KBr) (3650–3150), 1800, 1750, 1690, 1665, 1600, 1530, 1515, 1412, 1370, 1312, 1265, 1240, 1200, 1180, 1120, 1010, 745, 700 cm$^{-1}$.

$\delta$(CDCl$_3$) 2.13 (3H, s, COCH$_3$), 2.95(1H, d, J 17 Hz, 6$\beta$CH), 3.14 (2H, d, J 7 Hz, 9CH$_2$), 3.41 (1H, dd, J=17 and 3 Hz, 6$\alpha$CH), 3.48, 3.52 (4H, 2×s, 2×NCH$_2$), 3.73 (3H, s, CO$_2$CH$_3$), 4.74 (1H, t, J 7 Hz, 8CH), 4.97 (1H, s, 3CH), 5.57 (1H, d, J 3 Hz, 5°CH), 7.17–7.45 (9H, m, CH$_2$C$_6$H$_5$ CH$_2$C$_6$H$_4$NHCOCH$_3$).

DESCRIPTION 23

Benzyl 9-N-benzyl-N-(4-hydroxy-3-methoxy-benzyl) aminodeoxyclavulanate

Benzyl dichloroacetylclavulanate (4.07 g 10.2 mm) in dimethylformamide (75 cm$^3$) at 0° was treated with N-benzyl-N-(4-hydroxy-3-methoxybenzyl) amine (4.7 g; 1.9 equivalents) in dimethylformamide (20 cm$^3$), dropwise and stirred at 0° for ½ hr then at 20° for 1½ hrs. The reaction mixture was poured into ethylacetate (200 cm$^3$) and the organic phase washed with water (3×75 cm$^3$) and saturated brine (4×75 cm$^3$). The ethyl acetate phase was dried and evaporated in vacuo to yield a coloured foam. This foam was chromatographed on silica gel, eluting with ethylacetate-cyclohexane; 1:1. Fractions were collected containing the title compound and were evaporated in vacuo to yield 2.32 g (44%) of a colourless oil; Rf (SiO$_2$/ethylacetate: cyclohexane; 1:1)=0.66, detection by aqueous potassium permanganate spray. $\nu$(film) 3500 broad, 1800, 1750, 1695, 1610, 1602, 1512, 1450, 1430, 1380, 1302, 1270, 1230, 1180, 1155, 1120, 1080, 1032, 1015, 820, 800, 750, 700 cm$^{-1}$. $\delta$(CDCl$_3$) 2.85 (1H, d, J 17 Hz, 6$\beta$CH), 3.10 (2H, d, J7 Hz, 9CH$_2$), 3.31 (1H, dd, J17 and 31 Hz, 6$\alpha$CH), 3.35, 3.41 (4H, 2×s, NCH$_2$C$_6$H$_5$ and NCH$_2$C$_6$H$_3$(OH,OCH$_3$)), 3.74 (3H, s, OCH$_3$), 4.80 (1H, t, J 7 Hz, 8CH), 5.00 (1H, s, 3-CH), 5.09 (2H, s, OCH$_2$C$_6$H$_5$), 5.25 (1H, broad s, exchanges with D$_2$O-C$_6$H$_3$(OH, OCH$_3$), 5.51 (1H, d, J 3 Hz, 5$\alpha$CH), 6.71–6.78 (3H, m, protons in trisubstituted phenyl group), 7.20 (10H, broad s, 2×CH$_2$C$_6$H$_5$).

EXAMPLE 1

9-N-(2-Hydroxyethyl)aminodeoxyclavulanic acid p-Methoxybenzyl 9-[N-benzyl-N-(2-hydroxyethyl)-]aminodeoxyclavulanate (0.38 g) inethanol and tetrahydrofuran (1:1) (100 cm$^3$) was hydrogenated with 10% palladium on carbon as catalyst (0.15 g) for 23 hours. The mixture was filtered through celite and the clear filtrate evaporated in vacuo to yield a coloured oil. This oil was dissolved in ethyl acetate (100 cm$^3$) and extracted with water (50 cm$^3$). The aqueous extract was evaporated in vacuo to yield a pale yellow oil. This oil was chromatographed on a cellulose column, eluting with butanol/propan-2-ol/water 7:7:5. Fractions were collected containing only (1), Rf (SiO$_2$; butanol: propan-2-ol:water, 7:7:6)=0.20, detection by aqueous potassium permanganate spray. The combined fractions containing only 9-N-(2-hydroxyethyl)aminodeoxyclavulanic acid were evaporated in vacuo to yield a white solid, (50 mg); $\delta$(D$_2$O) 3.1. (1H, d, J 17 Hz, 6$\beta$-CH), 3.05–3.17 (2H, m, NCH$_2$CH$_2$OH), 3.57 (1H, dd, J 17 Hz and 3 Hz, 6$\alpha$-CH), 3.70–3.84 (4H, m, NCH$_2$CH$_2$OH, 9-CH$_2$), 4.80 (1H, t, J 8 Hz, 8CH), 4.99 (1H, s, 3-CH), 5.76 (1H, d, J 3 Hz, 5$\alpha$-CH). [CH$_3$CN was used as an internal standard, $\delta$CH$_3$CN=2.00]; $\nu$(KBr) 3000–3600, 1785, 1620 cm$^{-1}$.

EXAMPLE 2

9-N-Benzylaminodeoxyclavulanic acid

Benzyl 9-(N,N-dibenzylamino)deoxyclavulanate (0.43 g) in ethanol and tetrahydrofuran, 1:1 (75 cm$^3$) with 1 cm$^3$ water was hydrogenated with 5% palladium on carbon (0.43 g) as catalyst. The hydrogenation was carried out at 55 psi for 5 hours. The mixture was filtered through celite and the clear filtrate evaporated in vacuo to yield a coloured oil. This oil was dissolved in ethyl acetate (80 cm$^3$) and washed with water (3×30 cm$^3$). The combined aqueous extracts were evaporated in vacuo to yield a pale yellow oil. This oil was chromatographed on a cellulose column, eluting with butanol/propan-2-ol/water; 4:4:1. Fractions were collected containing 9-N-benzylaminodeoxyclavulanic acid, detection by aqueous potassium permanganate spray; Rf (SiO$_2$; butanol/propan-2-ol/water, 7:7:6)=0.45. The combined fractions were evaporated in vacuo to yield a solid. This solid was washed with ethanol and then dried to yield 9-N-benzylaminodeoxyclavulanic acid (36 mg). $\nu$(KBr) (3680–3150), (3100–2900), (2900–2300), 1800, 1694, 1610, 1460, 1400, 1305, 1190, 1020, 895, 755, 700 cm$^{-1}$; $\delta$(D$_2$O+5% DMSO D-6), 3.13 (1H, d, J 17 Hz, 6$\beta$-CH), 3.62 (1H, bd, J 17 Hz, 6$\alpha$-CH), 3.77 (2H, d, J 8 Hz, 9-CH$_2$), 4.22 (2H, s, CH$_2$C$_6$H$_5$), 4.84 (1H, t, J 8 Hz, 8-CH), 5.01 (1H, s, 3-CH), 5.77 (1H, bs, 5$\alpha$-CH), 7.48 (5H, s, C$_6$H$_5$).

The compound of this invention was produced as fine needles, (ie. in crystalline form). Crystalline 9-N-benzylaminodeoxyclavulanic acid is normally colourless. Chemical Analysis of the product indicated that the crystals contained water.

EXAMPLE 3

9-N-Ethylaminodeoxyclavulanic Acid

Benzyl 9-(N-benzyl-N-ethyl)aminodeoxyclavulanate [3.44 g; obtained by the reaction of benzyl trichloroacetylclavulanate (3 g) with 2 equivalents of N-benzylethylamine] in ethanol and tetrahydrofuran, 1:1 (100 cm$^3$) with 1 cm$^3$ water was hydrogenated with 10% palladium on carbon (1 g) as catalyst. The hydrogenation was carried out for 16 hours at atmospheric pressure. The mixture was filtered through celite and the clear filtrate evaporated in vacuo to yield an oil. This oil was dissolved in ethyl acetate (100 cm$^3$) and extracted with water (3×40 cm$^3$). The combined aqueous extracts were evaporated in vacuo to yield a pale yellow oil. This oil was chromatographed on a cellulose column, eluting with butanol/propan-2-ol/water; 4:4:1. Fractions were collected containing 9-ethylaminodeoxyclavulanic acid; Rf (SiO$_2$; Butanol/propan-2-ol/water; 7:7:6)=0.17, detection by aqueous potassium permanganate spray. The combined fractions were evaporated in vacuo to yield 9-N-ethylaminodeoxyclavulanic acid as a colourless crystalline solid (13% overall yield from benzyl trichloroacetylclavulanate); $\nu$(KBr) (3700–3250), (3200–2900), (2900–2600), (2600–2400), 1790, 1695, 1625, 1460, 1400, 1305, 1190, 1120, 1045, 1020, 900, 800, 745 cm$^{-1}$; $\delta$(D$_2$O) 1.22 (3H, t, J 7 Hz, —CH$_2$CH$_3$), 2.89–3.20 (3H, m, —CH$_2$CH$_3$ and 6$\beta$-CH), 3.57 (1H, broad d, J 17 Hz, 6$\alpha$-CH), 3.68 (2H, d, J 8 Hz, 9-CH$_2$), 4.78 (1H, t, J 8 Hz, 8-CH), 5.00 (1H, s, 3-CH), 5.73 (1H, broad s, 5$\alpha$-CH).

EXAMPLE 4

9-N-(dl-2-Hydroxypropyl)aminodeoxyclavulanic acid

Benzyl 9-[N-benzyl-N(dl-2-hydroxyporpyl)-]aminodeoxyclavulanate (3.5 mM) in ethanol and tetrahydrofuran, 1:1 (75 cm$^3$) with 1 cm$^3$ water was hydrogenated with 10% Palladium on carbon (0.9 g) as catalyst. The hydrogenation was carried out at atmosphereic pressure for 21 hours. Thin layer chromatography showed one major spot at Rf (SiO$_2$/butanol:propan-2-ol:water, 7:7:6)=0.24. Detection by potassium permanganate spray. The mixture was filtered through celite and the clear filtrate evaporated in vacuo to yield an oil. This oil was dissolved in ethyl acetate (100 cm$^3$) and extracted with water (3×50 cm$^3$). The combined aqueous extracts were evaporated in vacuo to yield a pale yellow oil. This oil was chromatographed on a cellulose column, eluting with butanol/propan-2-ol/water, 4:4:1. Fractions were collected containing 9-[N-(dl-2-hydroxypropyl)]aminodeoxyclavulanic acid, Rf (SiO$_2$butanol:propan-2-ol:water, 7:7:6)=0.24. The combined fractions were evaporated in vacuo to yield 9-N-(dl-2-hydroxypropyl)aminodeoxyclavulanic acid as a colourless oil in a 12% yield; δ(D$_2$O) 1.21 (3H, d, J 6 Hz, —CH$_2$CH(OH)C$\underline{H}_3$), 2.7–3.2 (3H, m, 6β-C$\underline{H}$, C$\underline{H}_2$CH(OH)CH$_3$), 3.57 (1H, broad d, J 17 Hz, 6α-C$\underline{H}$), 3.76 (2H, d, J 8 Hz, 9-C$\underline{H}_2$), 3.83–4.21 (1H, m, —CH$_2$C$\underline{H}$(OH)CH$_3$), 4.80 (1H, t, J 8 Hz, 8-C$\underline{H}$), 5.01 (1H, s, 3-CH), 5.75 (1H, broad s, 5α-C$\underline{H}$).

EXAMPLE 5

9-(4-Fluorobenzyl)aminodeoxyclavulanic acid

Benzyl 9-N-benzyl-N-(4-fluorobenzyl)aminodeoxyclavulanate (7 g of approximately 50% pure material) in 100 cm$^3$ tetrahydrofuran—ethanol (50%) plus 4 cm$^3$ water, was hydrogenated at 55 p.s.i. for 21 hours in the presence of 4 g palladium on carbon (10%). The mixture was filtered through celite and the clear filtrate evaporated to a coloured oil. The oil was dissolved in ethyl acetate (80 cm$^3$) and extracted with water (3×30 cm$^3$). The combined aqueous extracts were evaporated in vacuo to yield a coloured oil. This oil was chromatographed on a cellulose column, eluting with butanol/-propan-2-ol/water; 4:4:1. Fractions containing the title compound were collected, (detection by aqueous potassium permanganate spray; Rf (SiO$_2$butanol/propan-2-ol/water, 7:7:6)=0.63). The combined fractions were evaporated in vacuo to yield a colourless material which crystallised on the addition of ethanol and cooling. The crystals were washed with cold (0° C.) ethanol and dried to yield 9-(4-fluorobenzyl)aminodeoxyclavulanic acid (367 mg). ν(KBr) (3700–3120), (3120–2900), (2900–2650), (2650–2500), (2500–2300), 1805, 1695, 1580, 1515, 1470, 1410, 1340, 1303, 1283, 1230, 1185, 1165, 1045, 1008, 992, 895, 858, 835, 773 cm$^{-1}$.

EXAMPLE 6

9-N-(4-Methylbenzyl)aminodeoxyclavulanic acid

Benzyl 9-N-benzyl-N-(4-methylbenzyl)aminodeoxyclavulanate (10.6 g of approximately 50% pure material) in 100 cm$^3$ tetrahydrofuran - ethanol (50%) plus 4 cm$^3$ water was hydrogenated at 55 p.s.i. for 21 hours in the presence of 5 g palladium on carbon (10%). The mixture was filtered through celite and the clear filtrate evaporated in vacuo to a coloured oil. This oil was chromatographed on cellulos eluting with butanol/propan-2-ol/water: 4:4:1. Fractions containing the title compound were collected, detection by aqueous potassium permanganate spray: Rf (SiO$_2$; butanol/propan-2-ol/water, 7:7:6)=0.60. The combined fractions were evaporated in vacuo to yield an oil to which was added ethanol. On cooling a colourless crystalline solid formed. This was filtered off, washed with cold ethanol and dried to yield 85 mg of zwitterionic 9-N-(4-methylbenzyl)aminodeoxyclavulanic acid as fine needles.

ν(KBr) (3670 - 3150), (3150 - 2870), (2870 - 2500), (2500 - 2250), (1790, 1690, 1590, 1460, 1395, 1300, 1195, 1110, 1035, 1015, 1000, 990, 940, 892, 805, 748, 555, 485, 435 cm$^{-1}$.

EXAMPLE 7

9-N-(4-Methoxybenzyl)aminodeoxyclavulanic acid

Benzyl 9-N-benzyl-N-(4-methoxybenzyl)aminodeoxyclavulanate (1.4 g) in 100 cm$^3$ tetrahydrofuran - ethanol (50%) plus 2 cm$^3$ water was hydrogenated at 55 p.s.i. for 21 hours in the presence of 1 g palladium on carbon (10%). The reaction mixture was filtered through celite and the filtrate evaporated in vacuo to yield a coloured foam. This foam was chromatographed on cellulose eluting with butanol - isopropanol - water; 4:4:1. Fractions containing the title compound only were collected. Rf (SiO$_2$/butanol-isopropanol-water; 7:7:6)=0.60, detection by aqueous potassium permanganate spray. These fractions were evaporated in vacuo to yield a colourless residue. Trituration of the residue under cooled ethanol yielded solid zwitterionic 9-N-(4-methoxybenzyl)aminodeoxyclavulanic acid as fine needles, (33 mg).

ν(KBr) (3600), (3500 - 3150), (3150 -2880), (2880 - 2780), (2780 -2680), (2680 -2520), (2520 - 2250), 1790, 1695, 1600, 1517, 1470, 1400, 1305, 1255, 1200, 1184, 1125, 1030, 995, 950, 900, 840, 820, 767, 760, 575, 545, 445 cm$^{-1}$.

EXAMPLE 8

9-N-(4-Hydroxy-3-methoxybenzyl)aminodeoxyclavulanic acid

Benzyl 9-N-(4-benzoxy-3-methoxybenzyl)benzylaminodeoxyclavulanate (0.7 g of approximately 50% pure material) in tetrahydrofuran - ethanol (50%) 50 cm$^3$ plus 2 cm$^3$ water was hydrogenated at 55 p.s.i. for 15 hours in the presence of 0.5 g palladium on carbon (10%). The reaction mixture was filtered through celite and the filtrate evaporated in vacuo to yield a coloured oil. This oil was dissolved in ethyl acetate (50 cm$^3$) and extracted with water (2×25 cm$^3$). The combined aqueous extracts were evaporated in vacuo to yield a coloured foam. This foam was chromatographed on a cellulose column, eluting with butanol/propan-2-ol/water 4:4:1. Fractions containing the title compound were collected and evaporated in vacuo to yield 9-N-(4-hydroxy-3-methoxybenzyl)aminodeoxy-clavulanic acid as a white solid (30 mg). Rf (SiO$_2$/butanol-propan-2-ol-water; 7:7:6)=0.56. The p.m.r. spectrum was consistent with the desiredd product.

EXAMPLE 9

9-N-(4-Hydroxy-3-methoxybenzyl)aminodeoxyclavulanic acid

Benzyl 9-N-(4-hydroxy-3-methoxybenzyl)benzyl aminodeoxyclavulanate (2.27 g) in 80 cm$^3$ tetrahydrofuran-ethanol (50%) plus 2 cm$^3$ water, was hydrogenated at 55 psi for 6 hours in the presence of 2 g palladium on charcoal (10%). The mixture was filtered through celite and the clear filtrate evaporated in vacuo to yield a pale yellow foam. To this foam was added methanol (5 cm³), then to this solution was added dry acetone (70 cm³) and the resultant precipitated white solid filtered off and dried, yield 0.88 g. 0.83 g of this crude material was chromatographed on cellulose with butanol/propan-2-ol/water; 4:4:1. Fractions were collected containing the title compound and were evaporated in vacuo to yield a white solid. Propan-2-ol was added (20 cm³) followed by methanol (10 cm³) and the solution cooled (0° C.). The crystalline product was filtered off and washed with cold (0°) methanol and dried to yield 9-N-(4-hydroxy-3-methoxybenzyl)aminodeoxyclavulanic acid as fine needles (102mg). Rf (SiO$_2$/butanol-propan-2-ol-water; 7:7:6)=0.06.

EXAMPLE 10
9-N-Benzylaminodeoxyclavulanic acid

Benzyl 9-N,N-di-benzylaminodeoxyclavulanate (13 g) was dissolved in 60 cm³ tetrahydrofuran plus 50 cm³ of aqueous propan-2-ol (H$_2$O: IPA=2:5). To this was added 6 g of palladium on charcoal (10%) which had been previously washed with water (to neutral filtrate). The reaction mixture was hydrogenated at 55 psi for 6½ hours, filtered through celite (pH of the filtrate was 5.37) and washed with aqueous tetrahydrofuran (50%, 150 cm³) followed by aqueous ethanol (50%, 200 cm³). The filtrate from the final washing was collected separately and evaporated to yield a white solid. Ethanol was added (20 cm³) and cooled (0°), then filtered and washed with ice-cold ethanol, and dried in vacuo to yield 9-N-benzylaminodeoxyclavulanic acide as a finely crystalline solid (0.32 g). The main filtrate was evaporated and ethanol added (50 cm³) resulting in rapid crystallisation. The solid was filtered off and washed with ice-cold ethanol and dried in vacuo to yield 9-N-benzylaminodeoxyclavulanic acid as a very slightly off-white crystalline solid (1.57 g). The filtrate was again evaporated but this time ethanol was added (50 cm³). Cooling yielded fine crystals, which were filtered off and washed with ice-cold methanol, and dried in vacuo to yield the 9-N-benzylaminodeoxyclavulanic acid as a finely crystalline solid (0.25 g). The total yield was 2.14 g. (assuming the dibenzylamino compound was 90% pure this represents a yield of 30%).

The coloured residue was evaporated and redissolved in ethanol. This solution was applied to a cellulose column 180 cm×4½ cm and partially eluted with ethanol (50 to 70 cm³) and then with butanol/isopropanol/water; 4:4:1. Fractions were collected containing virtually only 9-N-benzylaminodeoxyclavulanic acid were evaporated and methanol added; the resulting fine crystals of the desired compound were filtered off and washed with cold methanol to yield further 67 mg.

$\nu$max (nujol) 3620, 3540, 3400 broad, 3200 broad, 2800 - 2500, 2500 - 2300, 1810, 1690, 1610, 1575, 1395, 1185, 1145, 1115, 1080, 1060, 1040, 1030, 1015, 1005, 990, 945, 895, 865, 850, 815, 790, 755, 700 cm$^{-1}$.

Cu K$\alpha$ radiation, 36 kV, 26 mA, scan speed ½° 2$\theta$/min, scanned 33°→20° 2$\theta$: Reflections at the following approx. angles 2$\theta$: 11.5, 13.5, 15.2, 15.8, 16.4, 17.25, 18.2, (broad), 19.5, 21.0, 21.8, 22.5, 23.1, 24.1, 24.3, 25.2, 25.5, 26.0, 27.5, 28.4, 28.9, 29.6 32.6, (major reflections underlined).

EXAMPLE 11
9-N-(4-Hydroxybenzyl)-aminodeoxyclavulanic acid

Benzyl 9-N(4-benzoxybenzyl) benzylamino deoxyclavulanate (4 g of approximately 50% pure material) in tetrahydrofuran (60 cm³) and aqueous propan-2-ol (50%; 50 cm³) was hydrogenated at 55 psi for 6½ hours in the presence of 2 g palladium on carbon (10%). The mixture was filtered through celite and the catalyst washed with aqueous ethanol (200 cm³). The filtrate was evaporated in vacuo to yield a coloured foam. The foam was dissolved in ethanol (10 cm³) and dry ether added (100 cm³), the resultant precipitate was filtered off and dried, dissolved in a small volume of ethanol and chromatographed on cellulose, eluting with ethanol (60 cm³) then butanol/propan-2-ol/water; (4:4:1). Fractions were collected containing the title compound (detection by aqueous potassium permanganate spray), Rf (SiO$_2$/butanol/propan-2-ol/water; 7:7:6)=0.67. Combined fractions were evaporated in vacuo to yield an oil, trituration with cold methanol yielded 9-N(4-hydroxybenzyl) aminodeoxyclavulanic acid as fine crystals; (4.7 mg).

$\nu$(nujol mul) 3575, 3350, 3175, 1780, 1695, 1620, 1580, 1520, 1310, 1200, 1125, 1105, 1075, 1050, 1020, 1005, 985, 895, 840, 750, 720 cm$^{-1}$.

EXAMPLE 12
9-N-(3,4-Dimethoxybenzyl)aminodeoxyclavulanate

Using the procedures of the foregoing Examples, hydrogenation of benzyl 9-N-(3,4-dimethoxybenzyl)aminodeoxyclavulanate yields zwitterionic 9-N-(3,4-dimethoxybenzyl)aminodeoxyclavulanate.

EXAMPLE 13
9-N-(4-Acetamidobenzyl)aminodeoxyclavulanic acid

Benzyl 9-N-(4-acetamidobenzyl)benzylaminodeoxyclavulanate (0.9 g) in tetrahydrofuran (50 cm³) and water (10 cm³) was hydrogenated at atmospheric pressure in the presence of 0.3 g palladium on carbon (10%) for 40 minutes. The mixture was filtered through celite and the catalyst washed with aqueous tetrahydrofuran (1:1, 100 cm³) and aqueous ethanol (1:1, 150 cm³). The clear filtrate was evaporated in vacuo, ethanol was added (20 cm³) and after cooling, colourless crystals were filtered off and dried to give 9-N-(4-acetamidobenzyl)aminodeoxyclavulanic acid (309 mg). The filtrate was evaporated in vacuo after which the addition of cold methanol yielded a further amount of the title compound (37 mg). Rf (SiO$_2$/butanol-propan-2-ol-water; 7:7:6)=0.45; detection by aqueous potassium permanganate spray. $\nu$(Nujol Mull) (3600 - 3440), 3380, (3350 - 3200), 3180, 3120, 2720, (2670 - 2520), 2450, (1805 - 1785), 1690, 1670, 1600, 1530, 1310, 1200, 1110, 1070, 1050, 1035, 1020, 1000, 990, 940, 895, 840, 750 cm$^{-1}$.

$\delta$(D$_2$O/DMSO) 2.01 (3H, s, CH$_3$CONH), 2.88 (1H, d, J 17 Hz, 6$\beta$C$\underline{H}$), 3.38 - 3.53 (3H, m, 6$\alpha$C$\underline{H}$, 9CH$_2$), 3.95 (2H, s, NCH$_2$), 4.61 - 4.75 (2H, m, 3C$\underline{H}$, 8C$\underline{H}$), 5.62 (1H, broad s, 5$\alpha$C$\underline{H}$), 7.30 - 7.56 (4H, ABq, J 9 Hz, CH$_2$C$_6$H$_4$-p-NHCOCH$_3$).

EXAMPLE 14
9-N-(2-Methoxybenzyl)aminodeoxyclavulanic acid

Benzyl 9-N-(2-methoxybenzyl)benzylaminodeoxyclavulanate (8 g of crude product) in tetrahydrofuran (100 cm³) and water (10 cm³) was hydrogenated in the presence of 10% palladium on carbon (1 g) at atmospheric pressure for 1½ hours. The mixture was filtered and the catalyst washed with aqueous tetrahydrofuran (100 cm³), the filtrate was evaporated in vacuo, to the residue was added ethyl acetate (150 cm³) and then washed with water (2×75 cm³). The combined aqueous extracts were evaporated in vacuo to a foam (3 g). This foam was chromatographed on cellulose eluting with butanol/propan-2-ol/water: 8:8:1. Fractions were collected containing the title compound, Rf (SiO₂/butanol-propan-2-ol-water; 7:7:6) 0.60 (detection by aqueous potassium permanganate spray). Combined fractions were evaporated in vacuo. On addition of cold ethanol colourless crystals formed; the crystals were filtered off and washed with cold ethanol and dried to yield 9-N-(2-methoxybenzyl)aminodeoxyclavulanic acid (140 mg). ν(Nujol mull) (3320 - 3220), (2750 - 2100), 1800, 1685, 1610, 1300, 1260, 1185, 1120, 1085, 1070, 1055, 1030, 1020, 1005, 935, 900, 775, 755, 745 cm⁻¹.

EXAMPLE 15

9-N-(2-Fluorobenzyl)aminodeoxyclavulanic acid

Benzyl 9-N-(2fluorobenzyl)benzylaminodeoxyclavulanate (0.35 g) in tetrahydrofuran (30 cm³) and water (3 cm³) was hydrogenated in the presence of 30% palladium on carbon (40 mg) at amtospheric pressure for 4 hours. A further quantity (40 mg) of the same catalyst was added and hydrogenolysis continued for 15 hours. The mixture was filtered and the catalyst washed with aqueous ethanol (50 cm³) was evaporated in vacuo. Addition of cold ethanol yielded 9-N-(2-fluorobenzyl)aminodeoxyclavulanic acid as a colorless crystalline solid (47 mg) Rf (SiO₂/butanol-propan-2-ol-water; 7:7:6)=0.51 (detection by aqueous potassium permanganate spray. ν(KBr), (3680 - 3140), (3140 - 2880), (2880 - 2500), (2500 - 2200), 1785, 1694, 1615, 1496, 1457, 1380, 1308, 1240, 1193, 1110, 1043, 1020, 900, 865 cm⁻¹. δ(D₂O) 3.05 (1H, d, J 17 Hz, 6βC$\underline{H}$), 3.54 (1H, dd, J 17 and 3 Hz 6αC$\underline{H}$), 3.72 (2H, d, J 7 Hz, 9C$\underline{H}_2$), 4.23 (2H, s, NC$\underline{H}_2$C₆H₄F), 4.77 (1H, t, J 7 Hz, 8C$\underline{H}$), 4.95 (1H, s, 3C$\underline{H}$), 5.70 (1H, d, J 3 Hz, 5αC$\underline{H}$), 7.05 - 7.48 (4H, m, CH₂C₆$\underline{H}_4$F).

EXAMPLE 16

Carboxymethyl 9-N-benzylaminodeoxyclavulanate

Benzyloxycarbonylmethyl 9-N-benzyloxycarbonyl-N-benzylaminodeoxyclavulanate (279 mg) was dissolved in tetrahydrofuran (20 ml) and water (2 ml) and hydrogenated at normal temperature and pressure over 10% palladium on carbon. After the reaction was complete (as judged by tlc) the catalyst was filtered off, washed well with aqueous tetrahydrofuran and the combined filtrated evaporated in vacuo to yield carboxymethyl 9-N-benzylaminodeoxyclavulanate.

The residue was triturated with acetone/ether to give carboxymethyl 9-N-benzylaminodeoxyclavulanate as a white solid which was filtered off and dried in a desiccator. $\nu_{max}$(Nujol) 1795, 1745, 1690, 1610 cm⁻¹.

EXAMPLE 17

Methyl 9-N-(4-acetamidobenzyl)aminodeoxyclavulanate hydrogen (L)-malate

Methyl 9-N-(4-acetamidobenzyl)benzylaminodeoxyclavulanate (0.5 g) in tetrahydrofuran (15 cm³) and water (5 cm³) was hydrogenated at atmospheric pressure for 2½ hours in the presence of 0.1 g palladium on carbon catalyst (30%) and malic acid (0.155 g; 1 equivalent). The mixture was filtered and the catalyst washed with aqueous tetrahydrofuran (10 cm³). The filtrate was evaporated in vacuo to an oil. This oil was dissolved in ethanol (10 cm³) and triturated with ether to yield a solid. This solid was washed with ether and dried in vacuo to yield methyl 9-N-(4-acetamidobenzyl)aminodeoxyclavulanate hydrogen L-malate as a solid (343 mg). ν(Nujol) 1800, 1745, 1690, 1670, 1600 cm⁻¹.

EXAMPLE 18

Methoxymethyl 9-N-benzylaminodeoxyclavulanate

9-N-Benzylaminodeoxyclavuianic acid (162 mg) in dimethylformaide (10 mls) at 20° was treated with clorodimethyl ether (42 mls, 1 equivalent) and stirred for 4–5 minutes (when tlc showed no further change). At this point the solution contains the hydrochloride salt of methoxymethyl 9-N-benzylaminodeoxyclavulanic acid; (Rf HCl salt 0.8 on SiO₂ using butanol:propanol:water 7:7:6). The mixture was poured into ethyl acetate (100 ml) and water (50 ml) and stirred vigorously while adding sodium bicarbonate (solid) until the pH was 9.5. The organic phase was washed with water (6×50 ml) and saturated brine (3×50 ml), dried (anhydrous magnesium sulphate) and evaporated to yield methoxymethyl 9-N-benzylaminodeoxyclavulanate as an oil (154 mg). (Rf, SiO₂/ethyl acetate 0.17).

$\nu_{max}$ (film)=3325 (broad), 1800, 1750, 1700, 745, 705 cm⁻¹.

EXAMPLE 19

Methoxymethyl 9-benzylaminodeoxyclavulanate hydrochloride

9-Benzylaminodeoxyclavulanic acid (0.4 g) in dimethylformamide (15 ml) was treated at room temperature with chlorodimethyl ether (1 equivalent) and stirred for 5 minutes, the evaporated in vacuo to yield an oil. This oil was dissolved in ethanol (5 ml) and added dropwise to diethyl ether (250 ml) with vigorous stirring. The resultant precipitate was filtered off, washed with dry diethyl ether, and dried in vacuo to yield methoxymethyl 9-benzylaminodeoxyclavulanate hydrochloride as a white solid (320 mg).

ν(Nujol) 2800-2460, 2460-2300, 1800, 1750, 1796, 750, 700 cm⁻¹.

δ(CD₃OD) values include: 3.10 (1H, d, J 17 Hz, 6β-CH), 3.43 (3H, s, OC$\underline{H}_3$), 3.74 (2H, d, J 7 Hz, 9-C$\underline{H}_2$), 4.15 (2H, s, C$\underline{H}_2$C₆H₅), 5.27 (2H, s, C$\underline{H}_2$OCH₃), 5.77 (1H, d, J 3 Hz, 5-C$\underline{H}$), 7.40 (5H, s, CH₂C₆$\underline{H}_5$).

EXAMPLE 20

Ethyl 9-N-benzylaminodeoxyclavulanate

A suspension of 9-N-benzylaminodeoxyclavulanic acid (576 mg) in methylene chloride (20 ml) was treated with a solution of triethyloxonium tetrafluoroborate (380 mg) in methylene chloride (20 ml) and stirred at room temperature for 3 hours until no further change was seen by tlc. The solvent was removed by evaporation to yield ethyl 9-N-benzylaminodeoxyclavulanate tetrafluoroborate. This residue was dissolved in aqueous sodium bicarbonate (roughly one equivalent) and extracted with methylene chloride (2+20 ml). The organic phase was washed with brine (20 ml), dried (anhydrous magnesium sulphate) and evaporated to yield ethyl 9-N-benzylaminodeoxyclavulanate as an oil (250 mgs). Rf=0.2 on SiO₂ using ethyl acetate.
νmax (film)=3300 (broad), 1800, 1745, 1695 cm⁻¹.

EXAMPLE 21

Benzyloxymethyl 9-N-benzylaminodeoxyclavulanate hydrochloride

9-N-Benzylaminodeoxyclavulanate (288 mg) was dissolved in dry dimethylformamide (15 ml) at room temperature and to this solution was added benzyloxymethyl chloride (157 mg) in dimethylformamide (1 ml). The reaction mixture was stirred at room temperature for a further four hours (tlc showed reaction was complete) and the solvent was removed in vacuo. The residue was dissolved in acetone, filtered through Celite and dry ether added. On cooling and scratching, benzyloxymethyl 9-N-benzylaminodeoxyclavulanate hydrochloride crystallised out and was collected by filtration (220 mg). $[\alpha]_D^{20} = +15.6°$ (1.0; MeOH); νmax (Nujol) 2725 (b), 1795, 1766, 1700 cm⁻¹; $\nu_{max}$ (KBr) 2940 (b), 2700–2840 (b), 1795, 1767, 1698 cm⁻¹; δ(CD₃OD) 3.08 (1H, d, J 17 Hz, 6β-C$\underline{H}$), 3.57 (1H, dd, J 3.5 and 17 Hz, 6α-C$\underline{H}$), 3.68 (2H, broad d, 9C$\underline{H}_2$), 4.11 (2H, s, ⁺NH₂C$\underline{H}_2$C₆H₅), 4.69 (2H, s, obscured by water peak, CH₂OC$\underline{H}_2$C₆H₅), 4.85 (1H, t, J 7 Hz, 8C$\underline{H}$), 5.23 (1H, s, 3-C$\underline{H}$), 5.38 (2H, s, CO₂C$\underline{H}_2$O), 5.71 (1H, d, J 3 Hz, 5-C$\underline{H}$), 7.23 (5H, s, aromatic —$\underline{H}$), 7.37 (5H, s, aromatic —$\underline{H}$).

EXAMPLE 22

4-Nitrobenzyloxymethyl 9-N-benzylaminodeoxyclavulanate hydrochloride

9-N-Benzylaminodeoxyclavulanate (0.4 g) in dry dimethylformamide (15 cm³) at room temperature was treated with 4-nitrobenzyloxymethylchloride (1 equivalent) and stirred for seven minutes. The solvent was evaporated in vacuo and acetone added (20 cm³) followed by petroleum spirit (80°–100°) and diethyl ether (1:1, 200 cm³), the mixture was cooled overnight and the resultant solid filtered off and washed with ether. Drying in vacuo afforded 4-nitrobenzyloxymethyl 9-N-benzylaminodeoxyclavulanate hydrochloride as an off-white solid (0.41 g). Rf (SiO₂/ethanol:chloroform, 1:4)=0.58. $\nu_{max}$ (film) 1805, 1755, 1700 cm⁻¹. δ(DMSO) 3.15 (1H, d, J 17 Hz, 6βC$\underline{H}$) 3.62 (1H, dd, J 17 and 3 Hz, 6-α-C$\underline{H}$) 3.5 (2H, broad m, 9-C$\underline{H}_2$), 4.03 (2H, broad s, sharp s on shaking with D₂O, NC$\underline{H}_2$C₆H₅), 4.86 (2H, s, C$\underline{H}_2$OCH₂C₆H₅NO₂), 4.96 (1H, t, J 7 Hz, 8C$\underline{H}$), 5.37 (1H, s, 3C$\underline{H}$), 5.45 (2H, s, CH₂OC$\underline{H}_2$C₆H₄NO₂), 5.70 (1H, d, J 3 Hz, 5α-C$\underline{H}$), 7.27–7.60 (7H, m, CH₂C₆H₅ and protons meta to nitro group of nitrobenzyl), 8.12 (2H, d, J 9 Hz, protons ortho to nitro group of nitrobenzyl), 9.72 (2H, broad s, exchanges with D₂O, N$\underline{H}_2$⊕).

EXAMPLE 23

9-N-Benzylaminodeoxyclavulanic acid p-toluene sulphonate

9-N-Benzylaminodeoxyclavulanic acid (288 mg) was suspended in benzyl alcohol (15 ml) and p-toluene sulphonic acid (190 mg) added to form the title compound.

EXAMPLE 24

Benzyl 9-N-benzylaminodeoxyclavulanate p-toluene sulphonate

Dicyclohexylcarbodiimide (206 mg) was added to the solution obtained in Example 23 and the mixture stirred at room temperature overnight. The solution was loaded onto a column of silica gel and the product obtained by gradient elution with chloroform/ethanol, finally eluting with 10:1. The title compound was obtained as a white solid on trituration with acetone/ether. $\nu_{max}$ (Nujol) 1810, 1750, 1700 cm⁻¹.

EXAMPLE 25

Ethyl 9-N-benzylaminodeoxyclavulanate p-toluene sulphonate

9-N-Benzylaminodeoxyclavulanic acid (288 mg) was suspended in ethanol (15 ml) and p-toluene sulphonic acid (190 mg) added to form the acid addition salt. Dicyclohexylcarbodiimide (206 mg) was added to the solution and the reaction mixture stirred for several hours at room temperature. The solvent was removed and the product purified by column chromatography on silica gel, eluting with butanol/propan-2-ol/water 4:4:1. Fractions containing the title compound were combined and evaporated; addition of ethanol and ether to the residue gave the product as a white solid which was filtered off and dried. ν(Nujol mull) 1810, 1750, 1700 cm⁻¹.

EXAMPLE 26

Phenacyl 9-N-benzylaminodeoxyclavulanate hydrobromide

9-N-Benzylaminodeoxyclavulanic acid (288 mg) in dimethylformamide (15 ml) was treated with phenacyl bromide (199 mg) and the resulting solution stirred at room temperature for 1½ hours. The dimethylformamide was evaporated in vacuo, the residue chromatographed on silica gel, and the title compound was eluted with chloroform/ethanol, 10:1. Evaporation of the fractions followed by trituration with acetone/ether gave the required salt as a pale yellow solid. $\nu_{max}$ (KBr) 1798, 1755, 1698 cm⁻¹.

EXAMPLE 27

Phenacyl 9-N-benzylaminodeoxyclavulanate hydroiodide

Phenacyl bromide (199 mg) was dissolved in acetone (2 ml) and a solution of sodium iodide (1.1 equivalent) in acetone (2 ml) added. An immediate precipitate of sodium bromide was obtained. After stirring the mixture for 10 minutes, the precipitate was filtered off and the filtrate added to a suspension of 9-N-benzylaminodeoxyclavulanic acid (288 mg) in dimethylformamide (15 ml). The solution was stirred at room temperature for 2 hours and the solvent removed. Fractionation of the crude product on silica gel, eluting with chloroform:ethanol, 10:1, gave the title compound. Work-up and trituration with acetone/ether gave the product as a pale yellow solid. $\nu_{max}$ (Nujol) 1800, 1750, 1695 cm⁻¹.

EXAMPLE 28

Lithium 9-N-carbobenzoxy-N-benzylaminodeoxyclavuanate

9-N-Benzylaminodeoxyclavulanic acid (1.15 g) in dimethylformamide (20 ml) containing one equivalent of lithium bicarbonate (544 mg; 10.8 ml 5% solution) was treated dropwise with a solution of benzylchloroformate (684 mg) in acetone (10 ml) at 0°. The reaction mixture was stirred at this temperature for 1 hour. The solvent was removed and the residue triturated with acetone/ether, the resulting white solid lithium 9-N-carbobenzoxy-N-benzylaminodeoxyclavulanate was filtered off and dried in a desiccator in vacuo (1.6 g). Rf (SiO$_2$:n-butanol:isopropanol:water; 7:7:6)=0.66; $[\alpha]_D^{20}$= +28.3° (C=1.6; water); $\nu_{max}$ (nujol) 1778, 1682, 1620 cm$^{-1}$, δ((CD$_3$)$_2$SO) 2.68 (1H, d, J 17.5 Hz, 6β-CH), 3.42 (1H, dd, obscured by water peak, 6α-CH), 3.8 (2H, d, J 7.5 Hz, 9-CH$_2$), 4.32 (2H, s, NCH$_2$C$_6$H$_5$), 4.52 (2H, m, 3-CH and 8-CH), 5.07 (2H, s, N.CO.O.CH$_2$), 5.52 (1H, d, J 3 Hz, 5-CH), 7.21 (5H, s, aromatic-H), 7.28 (5H, s, aromatic-H).

EXAMPLE 29

Methyl 9-N-carbobenzoxy-N-benzylaminodeoxyclavulanate

Lithium 9-N-Carbobenzoxy-N-benzylaminodeoxyclavulanate (428 mg) was dissolved in dimethylformamide (10 ml) and methyl iodide (710 mg) added. The reaction mixture was stirred at room temperature for 4 hours. The solvent was removed and the residue chromatographed on silica gel eluting with ethyl acetate:cyclohexane (1:1). The title compound was obtained after evaporation of the solvent as a colourless oil (244 mg). Rf (Ethylacetate-cyclohexane; 1:1)=0.75; $[\alpha]_D^{20}$= +13.21° (C=1.12; MeOH); $\nu_{max}$ (film) 1805, 1750, 1690 cm$^{-1}$; δ(CDCl$_3$) 2.86 (1H, d, J 17.5 Hz, 6β-CH), 3.42 (1H, dd, J 17.5 and 3 Hz, 6α-CH), 3.72 (3H (3H, s, CO$_2$CH$_3$), 3.96 (2H, d, J 7.5 Hz, CH.CH$_2$N), 4.44 (2H, s, NCH$_2$Ph), 4.67 (1H, bt, J 7.5 Hz, CHCH$_2$), 4.94 (1H, d, J 1.5 Hz, 3-CH), 5.16 (2H, s, CO$_2$CH$_2$Ph), 5.53 (1H, d, J 3 Hz, 5-CH), 7.22, 7.3 (10H, 2 x s, Ar-H).

EXAMPLE 30

Ethyl 9-N-carbobenzoxy-N-benzylaminodeoxyclavulanate

Ethyl iodide (780 mg) was added to a solution of lithium 9-N-carbobenzoxy-N-benzylaminodeoxyclavulanate (428 mg) in dimethylformamide (10 ml) containing about 2 drops water. The solution was allowed to stir at room temperature for seven hours. The solvent was removed by evaporation and the residue chromatographed on silica gel. The product was isolated by elution with ethyl acetate: cyclohexane; 1:1 and was obtained after evaporation of the solvent as a colourless oil (307 mg). Rf (ethyl acetate: cyclohexane; 1:1)=0.78; $[\alpha]_D^{20}$= +9.6° (C=1.38; MeOH); $\nu_{max}$ (film) 1802, 1745, 1695 cm$^{-1}$; δ(CDCl$_3$) 1.25 (3H, t, J 8 Hz, CH$_2$CH$_3$), 2.86 (1H, d, J 17.5 Hz, 6β-CH), 3.41 (1H, dd, J 17.5 Hz and 3 Hz, 6α-CH), 3.96 (2H, d, J 8 Hz, CHCH$_2$N), 4.17 (2H, q, J 8 Hz, CH$_2$CH$_3$), 4.43 (2H, s, NCH$_2$C$_6$H$_5$), 4.92 (1H, d, J 1.5 Hz, 3-CH), 4.67 (1H, bt, J 8 Hz, 8-CH), 5.17 (2H, s, CO.O.CH$_2$C$_6$H$_5$), 5.53 (1H, d, J 3 Hz, 5-CH), 7.23, 7.30 (10H, 2 x s, Ar-H).

EXAMPLE 31

Methyl 9-N-benzylaminodeoxyclavulanate hydrogen L-malate

Methyl 9-N-benzyloxycarbonyl-N-benzylaminodeoxyclavulanate (218 mg) in tetrahydrofuran (15 ml) and water (1 ml) was hydrogenated at N.T.P. in the presence of L-malic acid (67 mg) and 10% palladium on carbon (73 mg) for two hours. The catalyst was removed by filtration and the filtrate evaporated to dryness. Trituration with propan-2-ol/ether gave the title salt as an off-white solid. $\nu_{max}$ (Nujol) 1800, 1745, 1695, 1625 cm$^{-1}$.

EXAMPLE 32

Ethyl 9-N-benzylaminodeoxyclavulanate hydrogen L-malate

A solution containing ethyl 9-N-benzyloxycarbonyl-N-benzylaminodeoxyclavulanate (140 mg) and L-malic acid (42 mg) in tetrahydrofuran (15 ml) and water (1 ml) was hydrogenated over 10% palladium on carbon (45 mg) at N.T.P. for two hours. The catalyst was filtered off, washed with water and the filtrate evaporated. Trituration of the residue with propan-2-ol/ether gave the product as an off-white solid. $\nu_{max}$ (Nujol) 1800, 1745, 1695, 1630 cm$^{-1}$.

EXAMPLE 33

Benzyloxycarbonylmethyl 9-N-benzyloxycarbonyl-N-benzylaminodeoxyclavulanate

9-N-Benzyloxycarbonyl-N-benzylaminodeoxyclavulanic acid lithium salt (428 mg) was suspended in dimethylformamide (15 ml) and three drops of water added; benzyl bromoacetate (343 mg) was added to the resulting solution and the reaction mixture stirred at room temperature for five hours. Thin layer chromatography showed the reaction to be complete, the solvent was removed and the residue chromatographed on silica gel, eluting with ethyl acetate/cyclohexane (1:1). The combined fractions were evaporated in vacuo to yield a colourless oil (384 mg). Rf (SiO$_2$: ethyl acetate: cyclohexane, 1:1)=0.71; $[\alpha]_D^{20}$= +12.2° (C=1.16; MeOH); $\nu_{max}$ (film) 1805, 1750 (b), 1705 (sh), 1690 cm$^{-1}$; δ(CDCl$_3$) 2.86 (1H, d, J 17.5 Hz, 6β-CH), 3.38 (1H, dd, J 17.5 and 3 Hz, 6α-CH), 3.94 (2H, d, J 8 Hz, 9-CH$_2$). 4.44 (2H, s, NCH$_2$Ph), 4.65 (2H, s, CO$_2$CH$_2$CO$_2$), 4.74 (1H,bt, partially obscured by signal at 4.65), 5.04 (1H, d, J, 1.5 Hz, 3-CH), 5.15 (4H, s, NCO$_2$CH$_2$Ph and CH$_2$CO$_2$CH$_2$Ph), 5.52 (1H, d, J 3 Hz, 5-CH), 7.22, 7.29 (15H, 2×s, aromatic —H).

EXAMPLE 34

2-Hydroxyethyl 9-N-benzyloxycarbonyl-N-benzylaminodeoxyclavulanate

2-Iodoethanol (860 mg) was added to a solution of lithium 9-N-benzyloxycarbonyl-N-benzylaminodeoxyclavulanate (428 mg) in dimethylformamide (15 ml) and water (3 drops). The solution was stirred for 14 hours at room temperature and the solvent removed; the residue was purified by column chromatography on silica gel, eluting with ethyl acetate/cyclohexane, 1:1. The product was obtained as a colourless oil. Rf (SiO$_2$: ethyl acetate:cyclohexane, 1:1)=0.29; $\nu_{max}$ (film) 1800, 1745, 1700 cm$^{-1}$.

EXAMPLE 35

Methyl 9-N-benzylaminodeoxyclavulanate hydrogen succinate

Methyl 9-N-benzyloxycarbonyl-N-benzylaminodeoxyclavulanate (109 mg) was dissolved in tetrahydrofuran/methanol (10 ml) and hydrogenated at N.T.P. over 10% palladium on carbon (38 mg). The catalyst was filtered off and the solvent evaporated to yield the product as a gum. $\nu_{max}$ (film) 1800, 1740, 1695, 1615 cm$^{-1}$.

EXAMPLE 36

Methyl 9-N-benzylaminodeoxyclavulanate hydrogen L-tartrate

Methyl 9-N-benzyloxycarbonyl-N-benzylaminodeoxyclavulanate (87 mg) in tetrahydrofuran (10 ml) and water (1 ml) was hydrogenated at atmospheric pressure in the presence of (+)-tartaric acid (30 mg) and 10% palladium on carbon (30 mg) for ½ hour. The mixture was filtered through celite, the catalyst washed with water, and the filtrate was evaporated to dryness. Trituration of the residue with acetone/ether gave the product as a white solid. $\nu_{max}$ (Nujol) 1797, 1743, 1700, 1620 cm$^{-1}$.

EXAMPLE 37

Compositions a. 100 mg of sterile 9-N-benzylaminodeoxyclavulanic acid may be dissolved in 5 ml of sterile water for injection to yield an injectable solution.

b. 100 mg of sterile 9-N-benzylaminodeoxyclavulanic acid and sterile sodium amoxycillin equivalent to 250 mg pure free acid may be dissolved in 8 ml of sterile water for injection to yield an injectable solution.

c. 50 mg of sterile 9-N-benzylaminodeoxyclavulanic acid and sterile sodium amoxycillin equivalent to 250 mg pure free acid may be dissolved in 5 ml of sterile water for injection to yield an injectable solution.

Similar compositions may be prepared which contain 9-N-(4-acetamidobenzyl)aminodeoxyclavulanic acid 9-N-(4-hydroxybenzylamino)deoxyclavulanic acid or 9-N-(4-methoxybenzyl)aminodeoxyclavulanic acid in place of the 9-N-benzylaminodeoxyclavulanic acid.

Demonstration 1

In-vitro Activity

The MIC values for ampicillin alone and in 1 μg/ml or 5 μg/ml of the compounds of the Examples were determined by the microtitre method. The results were as follows:

| Compound of Example No. | Staphylococcus aureus Russell | | | Klebsiella aerogenes E70 | | | Proteus sp. C889 | | | E. coli JT 39 | | |
|---|---|---|---|---|---|---|---|---|---|---|---|---|
| | +0 | +1 | +5 | +0 | +1 | +5 | +0 | +1 | +5 | +0 | +1 | +5 |
| 1 | 62.5 | 0.3 | 0.01 | >500 | 3.1 | 1.5 | >500 | 125 | 4 | >500 | 8 | 8 |
| 2 | 500 | 0.08 | 0.01 | 1000 | 1.6 | 0.4 | 2000 | 2 | 0.5 | 2000 | 2 | 0.5 |
| 3 | 62 | 0.2 | — | >500 | 6.2 | 6.2 | >500 | 62 | 16 | >500 | 8 | 4 |
| 4 | 500 | 0.6 | 0.04 | 1000 | 3.1 | 1.6 | 2000 | 31 | 2 | 2000 | 16 | 4 |
| Sodium Clavulanate | 500 | 0.6 | 0.02 | 100 | 3.1 | 0.8 | 2000 | 62 | 4 | 2000 | 31 | 4 |
| 5 | >62.5 | 0.3 | <0.01 | >500 | 6.25 | 3.12 | >500 | 125 | 8 | >500 | 4 | 4 |
| 7 | >62.5 | 0.01 | <0.01 | >500 | 12.5 | 3.12 | >500 | 62.5 | 2 | >500 | 8 | 4 |
| 13 | >62.5 | 0.08 | — | >500 | 3.1 | 1.5 | >500 | 4 | 2 | >500 | 8 | 2 |

In-vivo Activity

The synergistic effect of the compounds of this invention in animals is demonstrated by the co-administration of the compound of Example 2 and amoxycillin (as the sodium salt) to test animals infected by E. coli JT 39. This microorganism produces considerable quantities of a β-lactamase which degrades amoxycillin so reducing its antibacterial effectiveness in-vivo. However when the compound of Example 2 is administered to the test animal at the same time as amoxycillin the inhibition of the β-lactamase allows the amoxycillin to exhibit its antibacterial activity. The following results were obtained when amoxycillin alone or together with the compound of Example 2 or sodium clavulanate was administered sub-cutaneously to mice infected by E. coli JT 39:

| Test Compounds | CD$_{50}$ (mg/kg × 2) |
|---|---|
| Sodium amoxycillin alone | 200 |
| Sodium amoxycillin + 2 mg/kg of compound of Example 2 | 3.3 |
| Sodium amoxycillin + 1 mg/kg compound of Example 2 | 8.7 |
| Sodium amoxycillin + 2 mg/kg of sodium clavulanate | 14.5 |
| Sodium amoxycillin + 1 mg/kg of sodium clavulanate | 58 |

(Sodium amoxycillin was prepared by dissolving amoxycillin trihydrate in a sodium carbonate/sodium bicarbonate buffer).

The compound of Example 2 was also effective in protecting amoxycillin from the β-lactamase of E. coli JT 39 in-vivo when administered orally but was less effective per given weight than when administered sub-cutaneously.

The compound of Example 2 was not observed to produce toxic effects during these tests.

Demonstration 2

Demonstration of Effectiveness as Synergist

The following approximate CD$_{50}$ values were obtained for amoxycillin in the presence of the compounds of certain Examples when administered sub-cutaneously 1 and 5 hours post infection against a peritoneal infection due to E. coli JT39.

| | CD$_{50}$ |
|---|---|
| Test 1 | |
| Amoxycillin alone | 1000 mg/kg × 2 |
| Amoxycillin + Comp Ex 2 at 2 mg/kg | 4.5 mg/kg × 2 |
| Amoxycillin + Comp Ex 2 at 1 mg/kg | 6.3 mg/kg × 2 |
| Amoxycillin + Comp Ex 7 at 2 mg/kg | 6.4 mg/kg × 2 |
| Amoxycillin + Comp Ex 7 at 1 mg/kg | 7.5 mg/kg × 2 |
| Amoxycillin + Comp Ex 9 at 2 mg/kg | 4.5–8 mg/kg × 2 |
| Amoxycillin + Comp Ex 9 at 1 mg/kg | 12 mg/kg × 2 |
| Cefazolin alone | 10.5 mg/kg × 2 |
| Test 2 | |
| Amoxycillin alone | 1000 mg/kg × 2 |
| Amoxycillin + Comp Ex 6 at 2 mg/kg | 3.1 mg/kg × 2 |
| Amoxycillin + Comp Ex 6 at 1 mg/kg | 8 mg/kg × 2 |
| Amoxycillin + Comp Ex 2 at 2 mg/kg | 4.5 mg/kg × 2 |
| Amoxycillin + Comp Ex 2 at 1 mg/kg | 8.5 mg/kg × 2 |
| Test 3 | |
| Amoxycillin alone | 1000 mg/kg × 2 |

| Compound | CD$_{50}$ |
|---|---|
| Amoxycillin + Comp Ex 13 at 2 mg/kg | 4.4 mg/kg × 2 |
| Amoxycillin + Comp Ex 2 at 2 mg/kg | 5.8 mg/kg × 2 |

Demonstration 3

Demonstration of Effectiveness as Anti-Bacterial

Mice were infected with staphylococcus aureus Russell (thigh lesion with 0.2 ml im) and thereafter were dosed subcutaneously at 1, 3 and 5 hours post infection with a solution of the test compound. The following results were obtained:

| Compound | Dosage (mg/kg) | Protection (%) |
|---|---|---|
| 9-N—Benzylaminodeoxyclavulanic acid | 5 | 69.8 |
| | 10 | 89.7 |
| | 20 | 99.3 |
| 9-N—p-Methoxybenzylaminodeoxy-clavulanic acid | 5 | 28.0 |
| | 10 | 80.8 |
| | 20 | 87.6 |
| Cloxacillin | 20 | 61.6 |
| | 50 | 91.7 |
| Cefazolin | 20 | 39.0 |
| | 50 | 71.2 |

The LD$_{50}$ of 9-N-benzylaminodeoxyclavulanic acid in mice is greater than 1000 mg/kg on intra peritoneal injection and greater than 500 mg/kg on sub-cutaneous administration.

What we claim is:

1. A compound of the formula (XI):

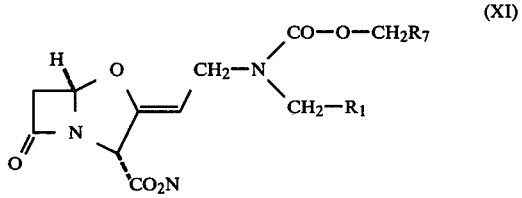

(XI)

a salt or a pharmaceutically acceptable ester thereof wherein R$_1$ is hydrogen, alkyl of up to 5 carbon atoms, cycloalkyl of 5 or 6 carbon atoms, hydroxyalkyl of up to 6 carbon atoms or a moiety of the sub-formula (a):

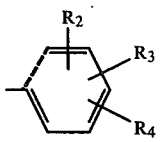

wherein R$_2$ is hydrogen, fluorine, chlorine, bromine, alkyl of 1–3 carbon atoms, alkoxyl of 1–3 carbon atoms, acyloxyl of 1–3 carbon atoms and no additional heteroatoms, hydroxyl, alkoxycarbonyl containing 1–3 carbon atoms in the alkoxy moiety or —N(R$_5$)CO.R$_6$—N(R$_5$)SO$_2$R$_6$ or —CO—NR$_5$R$_6$ wherein R$_5$ is hydrogen, alkyl of 1–3 carbon atoms, phenyl or benzyl and R$_6$ is alkyl of 1–3 carbon atoms, phenyl or benzyl; R$_3$ is hydrogen, fluorine, chlorine, alkyl of 1–3 carbon atoms, alkoxyl of 1–3 carbon atoms or acyloxyl of 1–3 carbon atoms and no additional heteroatoms; and R$_4$ is hydrogen, fluorine, chlorine, alkyl of 1–3 carbon atoms or alkoxyl of 1–3 carbon atoms and R$_7$ is a moiety of the sub-formula (a):

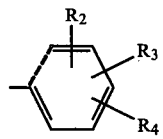

wherein R$_2$, R$_3$ and R$_4$ are as above defined.

2. A compound according to claim 1 wherein R$_7$ is phenyl.

3. A compound according to claim 1 in the form of an ester.

4. A compound according to claim 1 in the form of an alkali metal salt.

5. A compound according to claim 1 in the form of a lithium salt.

6. The compound which is methyl 9-N-carbobenzoxy-N-benzylaminodeoxyclavulanate.

7. The compound which is ethyl 9-N-carbobenzoxy-N-benzylaminodeoxyclavulanate.

8. The compound which is lithium 9-N-carbobenzoxy-N-benzylaminodeoxyclavulanate.

* * * * *